(12) United States Patent
Serda et al.

(10) Patent No.: US 10,881,612 B2
(45) Date of Patent: Jan. 5, 2021

(54) CATIONIC LIPOSOMES FOR CANCER IMMUNOTHERAPY

(71) Applicant: The Methodist Hospital, Houston, TX (US)

(72) Inventors: Rita Elena Serda, Pearland, TX (US); Ismail Mustafa Meraz, Pearland, TX (US)

(73) Assignee: The Methodist Hospital, Houston, TX (US)

( * ) Notice: Subject to any disclaimer, the term of this patent is extended or adjusted under 35 U.S.C. 154(b) by 28 days.

(21) Appl. No.: 15/754,206

(22) PCT Filed: Aug. 19, 2016

(86) PCT No.: PCT/US2016/047851
§ 371 (c)(1),
(2) Date: Feb. 21, 2018

(87) PCT Pub. No.: WO2017/035009
PCT Pub. Date: Mar. 2, 2017

(65) Prior Publication Data
US 2018/0243216 A1  Aug. 30, 2018

Related U.S. Application Data

(60) Provisional application No. 62/208,344, filed on Aug. 21, 2015.

(51) Int. Cl.
| | | |
|---|---|---|
| A61K 9/127 | (2006.01) | |
| A61K 38/18 | (2006.01) | |
| A61K 38/20 | (2006.01) | |
| C07K 14/475 | (2006.01) | |
| C07K 14/54 | (2006.01) | |
| A61K 31/7016 | (2006.01) | |
| C07K 17/02 | (2006.01) | |
| A61K 47/69 | (2017.01) | |
| A61K 47/54 | (2017.01) | |
| A61P 35/00 | (2006.01) | |

(52) U.S. Cl.
CPC ........ *A61K 9/1272* (2013.01); *A61K 31/7016* (2013.01); *A61K 38/208* (2013.01); *A61K 47/544* (2017.08); *A61K 47/554* (2017.08); *A61K 47/6911* (2017.08); *A61P 35/00* (2018.01); *C07K 17/02* (2013.01)

(58) Field of Classification Search
None
See application file for complete search history.

(56) References Cited

FOREIGN PATENT DOCUMENTS

| WO | WO-2013179014 A1 | 12/2013 |
|---|---|---|
| WO | WO-2017035009 A1 | 3/2017 |

OTHER PUBLICATIONS

Mazumder et al, PLOS Negl Trop Dis, 2011; vol. 5, No. 12, e1429, pp. 1-12.*
Ortega et al, Journal of Drug Targeting, 2009; 17(7): 496-501.*
Bal et al, Vaccine, 2011, vol. 29, pp. 1045-1052.*
Meraz et al, (PLOS One, 2014, 9 (4), e94703, published Apr. 15, 2014).*
Simpson-Abelson et al, Clinical Immunology, 2009, vol. 132, pp. 71-82.*
Hansen et al, (Cancer Immunology Immunotherapy, 2012, vol. 61, pp. 893-903.*
"International Application Serial No. PCT/US2016/047851 International Search Report dated Dec. 15, 2016", 3 pgs.
"International Application Serial No. PCT/US2016/047851, Written Opinion dated Dec. 15, 2016", 5 pgs.
Meraz, Ismail M., et al., "Adjuvant Cationic Liposomes Presenting MPL and IL-12 Induce Cell Death, Suppress Tumor Growth, and Alter the Cellular Phenotype of Tumors in a Murine Model of Breast Cancer", Mol. Pharmaceutics 2014, 11, (2014), 3484-3491.
Roeven, M W, "Efficient Nontoxic Delivery of PD-L1 and PD-L2 siRNA Into Dendritic Cell Vaccines Using the Cationic Lipid SAINT-18", J. Immunother., vol. 38, No. 4, (May 2015), 145-154.
Zom, G G, "Efficient Induction of Antitumor Immunity by Synthetic Toll-like Receptor Ligand-Peptide Conjugates", Cancer Immunol. Res., vol. 2, No. 8, (2014), 756-764.
"International Application Serial No. PCT US2016 047851, International Preliminary Report on Patentability dated Mar. 8, 2018", 7 pgs.

* cited by examiner

*Primary Examiner* — Bridget E Bunner
*Assistant Examiner* — Fozia Hamud
(74) *Attorney, Agent, or Firm* — Schwegman Lundberg & Woessner, P.A.

(57) ABSTRACT

Disclosed are positively-charged, cytotoxic nanoparticle compositions comprising immune modulators (such as the toll-like receptor (TLR)-4 ligand, monophosphoryl lipid (MPL)-A), and Interleukin (IL)-12)), which exhibit enhanced uptake by mammalian cancer cells, and cause increased cancer cell death and/or an increased release of cancer antigens following direct injection to populations of cancer or tumor cells. Also disclosed are nanoparticle-vectored, immunomodulatory compositions that stimulate antigen presenting immune cells and T cells, and support the development of anti-cancer immunity in mammalian hosts. The disclosed cationic liposomes represent an important advance in the area of cancer immunotherapeutics.

13 Claims, 8 Drawing Sheets

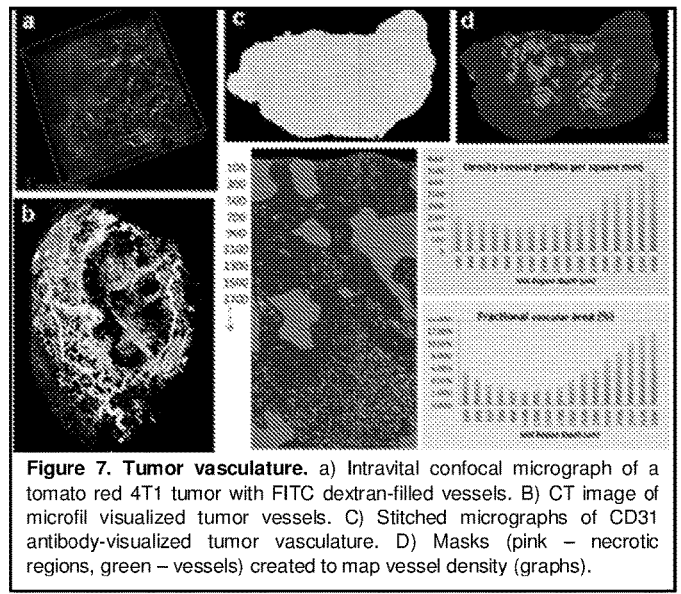

Figure 7. Tumor vasculature. a) Intravital confocal micrograph of a tomato red 4T1 tumor with FITC dextran-filled vessels. B) CT image of microfil visualized tumor vessels. C) Stitched micrographs of CD31 antibody-visualized tumor vasculature. D) Masks (pink – necrotic regions, green – vessels) created to map vessel density (graphs).

Fig. 7

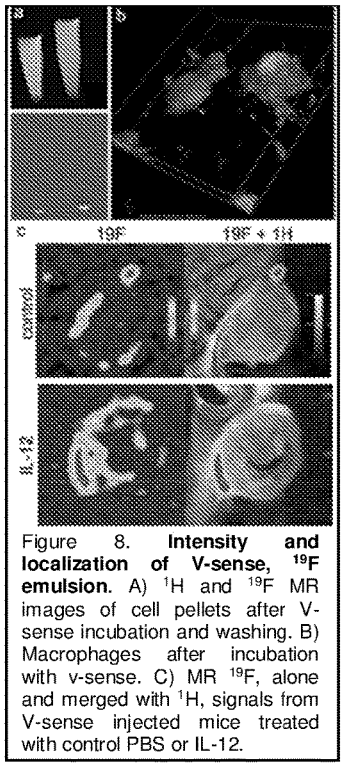

Fig. 8

Figure 8. Intensity and localization of V-sense, $^{19}F$ emulsion. A) $^1H$ and $^{19}F$ MR images of cell pellets after V-sense incubation and washing. B) Macrophages after incubation with v-sense. C) MR $^{19}F$, alone and merged with $^1H$, signals from V-sense injected mice treated with control PBS or IL-12.

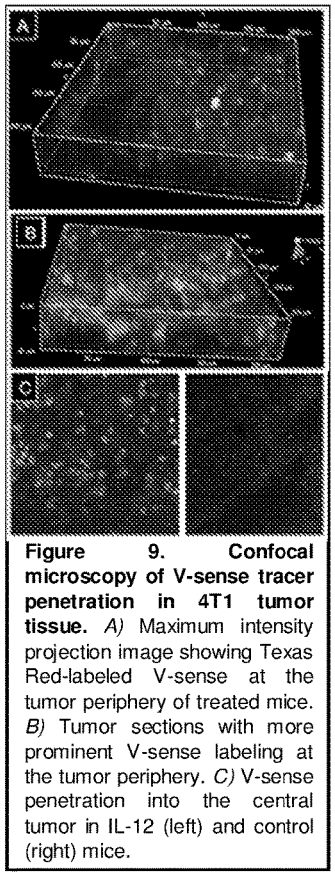

Fig. 9

Figure 9. Confocal microscopy of V-sense tracer penetration in 4T1 tumor tissue. *A)* Maximum intensity projection image showing Texas Red-labeled V-sense at the tumor periphery of treated mice. *B)* Tumor sections with more prominent V-sense labeling at the tumor periphery. *C)* V-sense penetration into the central tumor in IL-12 (left) and control (right) mice.

Fig. 10

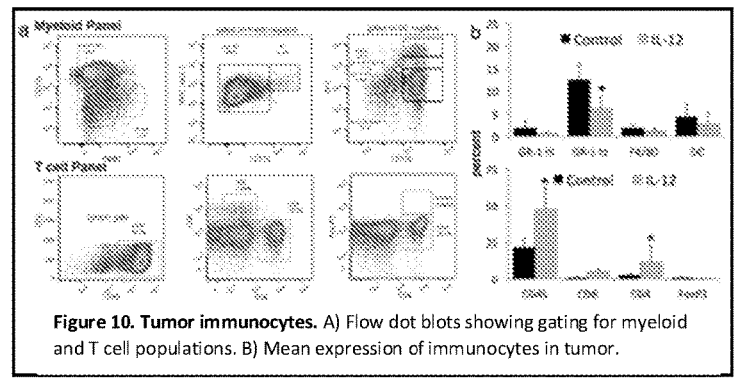

Figure 10. Tumor immunocytes. A) Flow dot blots showing gating for myeloid and T cell populations. B) Mean expression of immunocytes in tumor.

CATIONIC LIPOSOMES FOR CANCER IMMUNOTHERAPY

CROSS-REFERENCE TO RELATED APPLICATIONS

This application is a U.S. National Stage Filing under 35 U.S.C. 371 from International Application No. PCT/US2016/047851, filed on Aug. 19, 2016, and published as WO 2017/035009 on Mar. 2, 2017, which application claims the benefit of the filing date of U.S. application Ser. No. 62/208,344, filed on Aug. 21, 2015, the disclosures of which are incorporated by reference herein.

STATEMENT REGARDING FEDERALLY SPONSORED RESEARCH/DEVELOPMENT

This invention was made with government support under grant Nos. U54-CA151668 and U54-CA143837 awarded by the National Institutes of Health. The government has certain rights in the invention.

FIELD OF THE DISCLOSURE

The present disclosure relates to the fields of molecular biology, nanotechnology, immunotherapy, and medicine. Nanoparticle compositions have been developed for use in a variety of therapeutic and prophylactic indications. In particular, positively-charged, cytotoxic nanoparticles loaded with immune modulators exhibit uptake by mammalian cancer cells, resulting in cancer cell death and/or an increased release of cancer antigens following direct injection to a population of cancer cells. In exemplary embodiments, immune modulators, such as the toll-like receptor (TLR)-4 ligand monophosphoryl lipid (MPL)-A. and Interleukin (IL)-12, have been shown to stimulate antigen presenting immune cells and T cells, to support the development of anti-cancer immunity.

BACKGROUND

The goal of cancer immunotherapy is to boost or restore immune function for effective recognition of antigens associated with aberrant cells. The range of immunotherapy approaches is broad and includes antibody therapy (Lan et al., 2013), cytokine delivery to stimulate a passive immune response (Wayteck, et al., 2013; Jaime-Ramirez et al., 2011), ex viva stimulation of autologous immune cells that are subsequently administered to a patient (Phan et at, 2013), the use of toxic chemotherapy adjuvants for stimulating an immune response (Wan et al., 2012), and formulations with antigens combined with alum, emulsions, liposomes, immune stimulating complexes (Audibert, 2003), or polymeric nanoparticles (Craparo and Bondi, 2012).

Beyond protective transport and sustained release of therapeutics, nanoparticles have intrinsic properties that affect biological outcomes. As an example, the vaccine adjuvant alum, thought to function as a depot for sustained antigen release, induces cytotoxic effects leading to the release of uric acid and recruitment of immune cells to the site of injection (Kool et al., 2008). Alum favors T helper 2 (Th2) immune responses, which induce B cells to produce neutralizing antibodies (Rimaniol et al., 2007; Mori et al., 2012; Brewer, 2006). However, effective cancer immunotherapies require Th1 cytokines to arrest tumor growth, specifically IFN-γ and TNF-α (Braumuller et al., 2013).

Similar to alum, cationic liposomes have inherent cytotoxicity, inducing cell death and stimulating immune cell infiltration to the site of injection or accumulation. In contrast to alum, which relies on surface absorption for binding of MPL, liposomes incorporate MPL into the lipid bilayer. Previously, it was reported that MPL-liposomes suppress tumor growth in a 4T1 immune competent murine model of breast cancer, unlike an equivalent dose of free MPL (Meraz et al., 2014). In addition to recruiting and activating immune cells, tumor cell damage caused by the cationic liposomes is proposed to release endogenous tumor antigens, directing the immune response against cancer cells. The large pool of endogenous tumor antigens creates an array of epitopes for immune recognition. The adjuvant effects of cationic liposomes are supported by Yan et al. (2007) who demonstrated by microarray mRNA analysis that DOTAP liposomes up-regulate chemokines, including CCL2, CCL3, and CCL4, in dendritic cells (DC). Barnier-Quer et al. (2013) demonstrated that incorporation of cholesterol in the bilayer of cationic liposomes enhances their adjuvant effect. Using porous silicon microparticles, it was previously shown that particle presentation of adsorbed MPL increases particle uptake by DC; elevated DC expression of co-stimulatory and major histocompatibility complex (MHC) class I and II molecules; increased migration of DC to the draining lymph node; and enhanced associations between DCs presenting the ovalbumin peptide SIINFEKL and T cells from OT-1 mice (Meraz et al., 2012).

SUMMARY

The present disclosure overcomes limitations in the art by providing, in an overall and general sense, compositions comprising positively-charged, cytotoxic nanoparticles loaded with immune modulators for use in a variety of diagnostic and therapeutic indications. In one embodiment, the disclosed cationic liposomes exhibit an enhanced uptake by mammalian immune and cancer cells, which resulted in cancer cell death and/or an increased release of cancer antigens following direct injection of the liposomes into a population of cancer cells. Loading of these positively-charged, cytotoxic nanoparticles with immune modulators, such as one or more pattern recognition receptors including, without limitation, one or more toll-like receptor (TLR) ligands (e.g., ligands of TLR-2. TLR-3, TLR-4, TLR-5, TLR-6, TLR-7, TLR-8, or TLR-9), one or more C-type lectin (CLR) receptors, or one or more NOD-like receptors (NLR)); one or more distinct lipids, and a Type I cytokine, e.g., an interleukin, stimulates antigen presenting immune cells and T cells, and supports development of anticancer immunity when administered to a mammal. In one embodiment, the TLR ligand includes a ligand of TLR4 (bacterial outer wall) (e.g., LPS or MPL-A), TLR2 (e.g., microbial cell wall including but not limited to peptidoglycan, lipoteichoic acid and lipoprotein, lipoarabinomannan, zymosan). TLR7/8 (e.g., viral infection: single-stranded RNA or R848), TLR9 (e.g., microbial DNA: unmethylated CpG oligodeoxynucleotides (ODNs); TLR3 (e.g., double-stranded RNA, viral infection: Poly(I:C)), or TLR5 (e.g., flagellin; gram positive and negative bacteria). In one embodiment, the cytokine includes but is not limited to one or more of IL-12, IL-1, IL-6, IL-8, IL-18, IL-21, TNF-alpha, or interferon gamma. If the cationic liposome comprises two or more distinct lipids, one of the lipids is cationic, e.g., DOTAP is a cationic lipid, and at least one of the others is non-cationic, e.g., DPPC or DSPC). Ratios of the two or more distinct lipids can vary, for example, for two distinct lipids, the ratio of a non-cationic lipid. e.g., neutral lipid, to the cationic lipid may be x:1 wherein x>1, x=1 or x:1 where x<1. In one embodiment, x>1. Values for x are not necessarily whole numbers. In one embodiment, the liposome has three distinct components, one of which enhances the stability of the liposome (e.g., a stabilizing component such as cholesterol or disulfide-linked deoxyribonucleotides (ODNs)). For example, non-cationic lipid:stabilizing component:cationic lipid ratios may include x:z:1, wherein x and z independently are each >1. Values for x and z are not necessarily whole numbers. In one embodiment, x and z, independently are 1.5, 2, 2.5, 3, 3.5, 4, 4.5, 5, 5.5, 6, 7, 8, 9, 10, 11, 12, 13, 14, 15, or 20. In one embodiment, a range of values for the non-cationic lipid is from 5 to 10. In one embodiment, a range of values for the stabilizing component is from 1 to 5. In one embodiment, a range of values for the cationic lipid is from 1 to 5. In one embodiment, the numerical values in the ratios for non-cationic lipid:stabilizing component:cationic lipid are mole percents that add up to 100 or 10, e.g., 70:20:10 or 8:1:1. In one embodiment, where the numerical values add up to 100, the stabilizing component may have a value from 5 to 35. e.g., 10, 20 or 30. In one embodiment, where the numerical values add up to 100, the cationic lipid may have a value from 5 to 55 or more, e.g., 10, 20, 30, 40, or 50. In one embodiment, where the numerical values add up to 10, the non-cationic lipid may have a value from 3 to 8. In one embodiment, where the numerical values add up to 10, the stabilizing component may have a value from 1 to 5. In one embodiment, where the numerical values add up to 10, the cationic lipid may have a value from 1 to 5.

In one embodiment, the present disclosure provides cancer vaccine formulations that comprise cationic liposomes presenting one or more immunomodulators either on the surface of, or within the body of, the nanoparticles. The resulting compositions facilitate multifunctional vector vaccines, the ultimate outcome of which is the in situ presentation of one or more tumor antigens (or immunomodulatory agents including one or more "checkpoint" regulators such as PD-1 and CTLA-4 inhibitors, one or more small molecules, FAB fragments, nucleic acids, antibodies, and such like) which facilitate induction of tumor-specific immunogenicity in an animal.

In certain aspects, the compositions may further optionally include at least one additional agent, including, without limitation, at least one penetration enhancer, at least one therapeutic and/or chemotherapeutic agent, at least one targeting moiety, and/or at least one or more surface-exposed, surface-bound, surface expressed, or surface contained targeting moieties, either alone, or in combination with one or more adjuvanting and/or immunomodulatory or immunostimulatory components, or such like.

In related embodiments, the disclosure also provides therapeutic and/or diagnostic kits including one or more of the compositions disclosed herein, typically in combination with one or more pharmaceutically-acceptable carriers, one or more devices for administration of the compositions to a subject of interest, as well as one or more instruction sets for using the composition in the prevention, the diagnosis, or the treatment of a mammalian condition, disease, disorder, trauma, and/or dysfunction, including, without limitation, one or more cancers, tumors, and such like.

Also provided are methods for providing an active agent to a mammalian dendritic cell comprising administering to the subject, an effective amount of one or more of the positively-charged, cytotoxic nanoparticle-based compositions disclosed herein. In certain embodiments, the subject is at risk for, diagnosed with, or suspected of having one or more abnormal conditions, including, for example, one or more cancers, or other hyperproliferative disorders.

The disclosure also provides a method for administering an active agent to one or more cells, tissues, organs, or systems of a mammalian subject in need thereof. The method generally involves providing to a mammalian subject in need thereof, one or more of the compositions disclosed herein in an amount and for a time effective to administer the active agents contained with the positively-charged, cytotoxic nanoparticles to one or more selected tissues, organs, systems, or cells within or about the body of the subject. In particular embodiments, the subject is a human, and the composition comprises positively-charged, cytotoxic nanoparticles adapted and configured to localize to at least a first target site within or about the body of a human patient to which the active agent is being administered.

In certain methods, the cationic nanoparticle vaccine components disclosed herein may be adapted and configured to bypass or "cross" a biological barrier selected from the group consisting of a hemo-rheology barrier, a reticuloendothelial system barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier, or any combination thereof.

In certain embodiments, the cationic nanoparticle compositions may be formulated for pharmaceutical administration, such as in a suspension that includes a plurality of cationic nanoparticles, together with one or more adjuvants, active ingredients, therapeutics, diagnostic reagents, or any combination thereof.

As noted herein, the cationic nanoparticle compositions of the present disclosure may be administered to the subject through any one or more conventional methods for administration, including, without limitation, orally, intranasally, intravenously, subcutaneously, or by direct injection to one or more cells or one or more tissues within or about the body of the subject.

As further described herein, in certain applications, it may be desirable to contact a population of cells obtained from a subject ex vivo with the cationic nanoparticle compositions disclosed herein, and then, subsequently, to reintroduce the resulting contacted cells into the body of the subject. Such ex vivo therapy is particularly contemplated to be useful in introducing the disclosed cationic nanoparticles to populations of cancer cells, followed by addition of human dendritic cells to the apoptotic/necrotic cancer cells, allowing the active ingredients to be contacted with the cells, and then reintroducing the cells back into the body of the animal. In one embodiment, the cells extracted for such ex vivo manipulation will be those of the actual patient undergoing treatment.

FIGS. 3A-D. Impact of MPL-liposomes on tumor growth. A) BALB/c mice bearing 4T1 tumors were treated with two weekly intratumoral injections of control or MPL liposomes beginning on Day 12 after intramammary injection of tumor cells (n=5/group; tumor approximately 200 mm$^3$). Caliper-derived tumor measurements were taken every 2-4 days (***p=0.0001 compared to vehicle control; ### p<0.0001 compared to liposome control). B) BALB/c mice bearing 4T1 tumors were also treated with two weekly intratumoral injections of free or liposome-encapsulated MPL beginning on Day 13 after intramammary injection of tumor cells (n=3-5/group), with caliper-derived tumor measurements presented (*p<0.05 compared to vehicle control: # p<0.05 compared to MPL: reprinted with permission from Public Library of Science[13]. C) IVIS imaging of tumor cell luciferase expression in mice following intraperitoneal injection with luciferin (150 mg/kg) before and after liposome treatment. D) Mean weight of excised tumors on Day 25.

FIGS. 4A-E. Influence of IL-12 on the therapeutic efficacy of adjuvant liposomes. A) BALB/c mice bearing 4T1 tumors were treated with two weekly intratumoral injections of free or liposome-encapsulated MPL beginning on Day 10 after intramammary injection of tumor cells (n=5/group). Caliper-derived tumor measurements are presented (***p<0.001 compared to vehicle control; ###p<0.001 compared to MPL liposomes, ++p<0.01 compared to IL-12). B) IVIS imaging of tumor cell luciferase expression in mice following intraperitoneal injection with luciferin (150 mg/kg) before and after liposome treatment. C) Photograph of excised tumors from three randomly selected mice from each group. D) Mean weight of excised tumors on Day 23. E) Serum cytokine levels in control and liposome-treated mice five hr post injection, based on ELISA.

Figure 5:
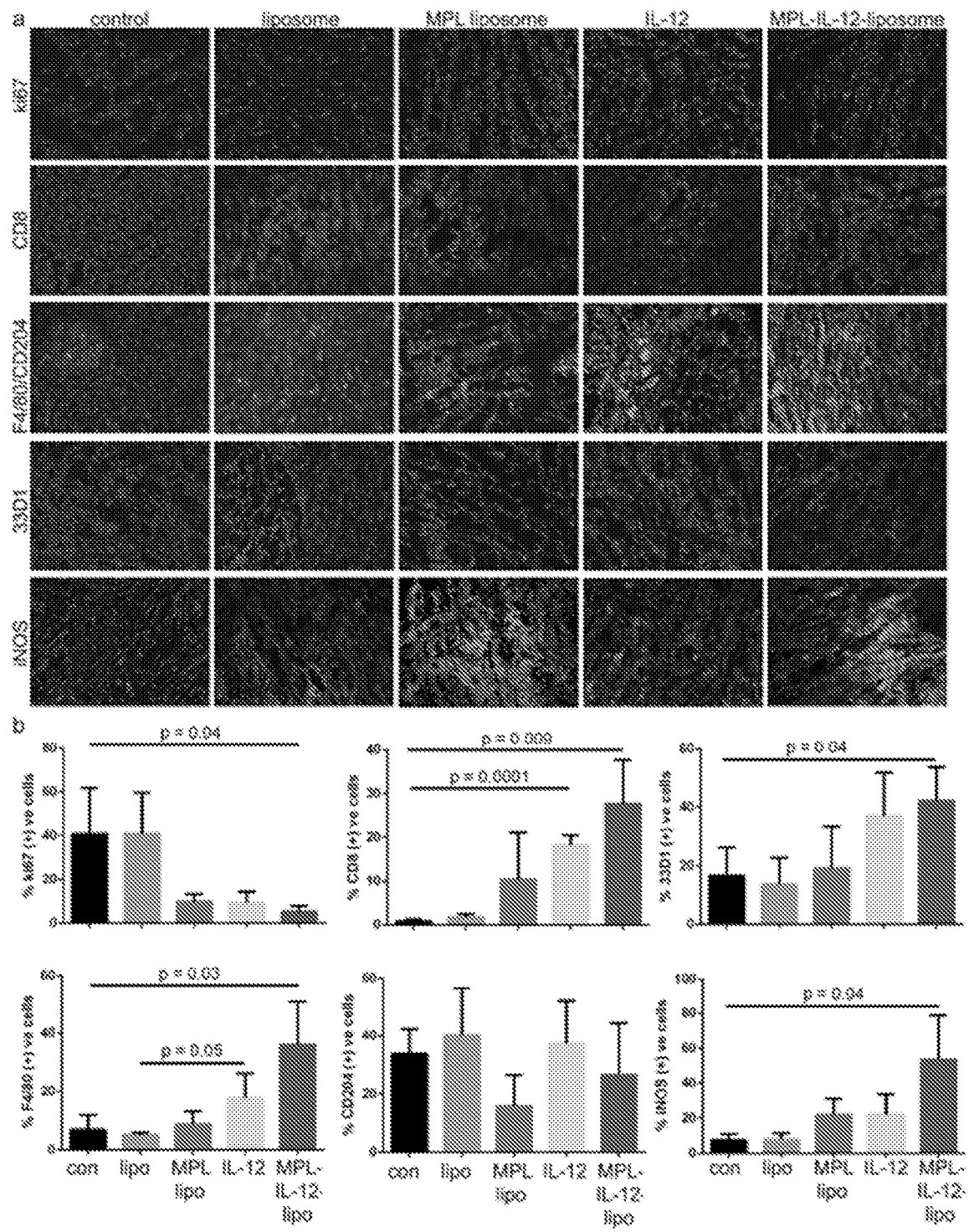

FIGS. 5A-B. Cellular phenotype of tumors following adjuvant nanoparticle therapy. A) Immunofluoresence staining of tumor sections from mice two weeks after initiation of liposome or IL-12 therapy [nuclei blue (DAPI), Ki67 red. CD8 red, F4/80 green, CD204 red, 33D1 red, iNOS green]. B) Percentage of immune cells in tumors based on manual, blinded cell counts in five randomly selected (based on DAPI staining) regions of interest.

Figure 6:
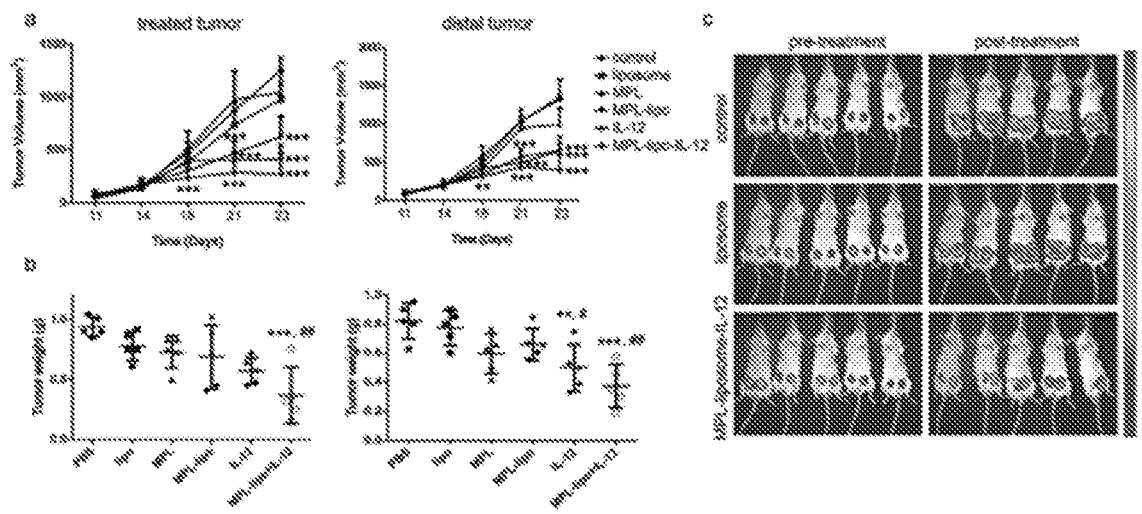

FIGS. 6A-C. Impact of therapy on distal untreated tumor growth. BALB/c mice were injected with 4T1 cells in each inguinal fat pad (n=5/group). When tumors were palpable, single tumors were treated by intramammary injection of liposomes, MPL or IL-12 twice at weekly intervals. A) Caliper measurements of treated and distal tumors ( p<0.01. * p<00.001, compared to vehicle control). B) Gross weights of excised tumors on Day 23 (p<0.01. *p<0.001 compared to vehicle control; # p<0.05. ## p<0.01 compared to liposome control). C) IVIS imaging of tumor cell luciferase activity in select BALB/c groups on Day 23.

FIGS. 7A-D. Tumor vasculature. A) Intravital confocal micrograph of a tomato red 4T1 tumor with FITC dextran-filled vessels. B) CT image of microfil visualized tumor vessels. C) Stitched micrographs of CD31 antibody-visualized tumor vasculature. D) Masks (pink—necrotic regions, green—vessels) created to map vessel density (graphs).

FIGS. 8A-C. Intensity and localization of V-sense, $^{19}$F emulsion. A) $^1$H and $^{19}$F MR images of cell pellets after V-sense incubation and washing. B) Macrophages after incubation with v-sense. C) MR $^{19}$F, alone and merged with $^1$H, signals from V-sense injected mice treated with control PBS or IL-12.

FIGS. 9A-C. Confocal microscopy of V-sense tracer penetration in 4T1 tumor tissue. A) Maximum intensity projection image showing Texas Red-labeled V-sense at the tumor periphery of treated mice. B) Tumor sections with more prominent V-sense labeling at the tumor periphery. C) V-sense penetration into the central tumor in IL-12 (left) and control (right) mice.

FIGS. 10A-B. Tumor immunocytes. A) Flow dot blots showing gating for myeloid and T cell populations. B) Mean expression of immunocytes in tumor.

DETAILED DESCRIPTION

Unless defined otherwise, all technical and scientific terms used herein have the same meaning as commonly understood by one of ordinary skill in the relevant arts. Although any methods and compositions similar or equivalent to those described herein can be used in the practice or testing of the present disclosure, including the methods and compositions are described herein. Singleton and Sainsbury (1994) and Hale and Margham (1991) are examples of references that provide one of ordinary skill with the general meaning of many of the terms used herein. Each of these references is specifically incorporated herein in its entirety by express reference thereto. For purposes of the present invention, the following terms are defined below for sake of clarity and ease of reference:

In accordance with long-standing patent law convention, the words "a" and "an," when used in this application (including in the appended claims), denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert(s), or such like, or a combination thereof that is pharmaceutically acceptable for administration to the relevant animal or acceptable for a therapeutic or diagnostic purpose, as applicable.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "effective amount." as used herein, refers to an amount that is capable of treating or ameliorating a disease or condition or otherwise capable of producing an intended therapeutic effect.

The terms "for example" or "e.g.," as used herein, are used merely by way of example, without limitation intended, and should not be construed as referring only those items explicitly enumerated in the specification.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

As used herein, the term "epitope" refers to that portion of a given immunogenic substance that is the target of, i.e., is bound by, an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, for example, Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

As used herein, "heterologous" is defined in relation to a predetermined referenced DNA or amino acid sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polypeptides or polynucleotides, sequences that have the same essential structure, despite arising from different origins. Typically, homologous proteins are derived from closely related genetic sequences, or genes. By contrast, an "analogous" polypeptide is one that shares the same function with a polypeptide from a different species or organism, but has a significantly different form to accomplish that function. Analogous proteins typically derive from genes that are not closely related.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, an isolated peptide in accordance with the invention in one embodiment does not contain materials normally associated with that peptide in its in situ environment.

As used herein, the term "kit" may be used to describe variations of the portable, self-contained enclosure that includes at least one set of reagents, components, or pharmaceutically-formulated compositions to conduct one or more of the diagnostic methods of the invention. Optionally, such kits may include one or more sets of instructions for use of the enclosed compositions, such as, for example, in a laboratory or clinical application.

As used herein, "mammal" refers to the class of warm-blooded vertebrate animals that have, in the female, milk-secreting organs for feeding the young. Mammals include without limitation humans, apes, many four-legged animals, whales, dolphins, and bats. A human is an exemplary mammal.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, the term "nucleic acid" includes one or more types of: polydeoxyribonucleotides (containing 2-deoxy-D-ribose, polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snoRNA), small nuclear RNA (snRNA), small temporal RNA (stRNA), and the like, as well as any combinations thereof.

As used herein, the term "patient" (also interchangeably referred to as "host" or "subject") refers to any host that can serve as a recipient of one or more of the therapeutic or diagnostic formulations as discussed herein. In certain aspects, the patient is a vertebrate animal, which is intended to denote any animal species (e.g., a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The phrase "pharmaceutically-acceptable" refers to molecular entities and compositions that do not produce an allergic or similar untoward reaction when administered to a human, and in particular, when administered systemically. The preparation of an aqueous composition that contains one or more active ingredients is well understood by those of ordinary skill in the pharmaceutical arts. Typically, such compositions are prepared as injectables, either as liquid solutions or as suspensions. Alternatively, they may be prepared in solid form suitable for solution or suspension in liquid prior to injection.

As used herein, "pharmaceutically-acceptable salt" refers to a salt that retains the desired biological activity of the parent compound and does not impart any undesired toxicological effects. Examples of such salts include, but are not limited to, acid-addition salts formed with inorganic acids, for example, hydrochloric acid, hydrobromic acid, sulfuric acid, phosphoric acid, nitric acid, and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, the term "polypeptide" is intended to encompass a singular "polypeptide" as well as plural "polypeptides." and includes any chain or chains of two or more amino acids. Thus, as used herein, terms including, but not limited to "peptide," "dipeptide," "tripeptide." "protein," "enzyme." "amino acid chain." and "contiguous amino acid sequence" are all encompassed within the definition of a "polypeptide." and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp). Cysteine (C; Cys), Glutamine (Q; Gin), Glutamic Acid (E: Glu), Glycine (G; Gly). Histidine (H; His). Isoleucine (I; Ile), Leucine (L; Leu), Methionine (M: Met). Phenylalanine (F; Phe). Proline (P; Pro), Serine (S; Ser), Threonine (T; Thr), Tryptophan (W; Trp), Tyrosine (Y; Tyr), Valine (V: Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, the terms "prevent." "preventing." "prevention," "suppress." "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is generally intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

"Purified," as used herein, means separated from many other compounds or entities. A compound or entity may be partially purified, substantially purified, or pure. A compound or entity is considered pure when it is removed from substantially all other compounds or entities. e.g., is at least about 90%, at least about 91%, 92%, 93%, 94%, 95%, 96%, 97%, 98%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "subject," as used herein, describes an organism, including mammals such as primates, to which treatment with the compositions according to the present invention can be provided. Mammalian species that can benefit from the disclosed methods of treatment include, but are not limited to, apes: chimpanzees; orangutans; humans; monkeys: domesticated animals such as dogs and cats; livestock such as horses, cattle, pigs, sheep, goats, and chickens; and other animals such as mice, rats, guinea pigs, and hamsters.

As used herein, the term "substantially free" or "essentially free" in connection with the amount of a component refers to a composition that contains less than about 10 weight percent, less than about 5 weight percent, aor less than about 1 weight percent of a compound. In some embodiments, these terms refer to less than about 0.5 weight percent, less than about 0.1 weight percent, or less than about 0.01 weight percent.

The term "substantially complementary." when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and may be greater than about 85 percent complementary to the corresponding target sequence to which the nucleic acid specifically binds. In certain aspects, as described above, it will be desirable to have even more substantially complementary nucleic acid sequences for use in the practice of the disclosure, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid or polypeptide sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. Exemplary default parameters for the GAP program include: (1) a unary comparison matrix (containing a value of 1 for identities and 0 for non-identities) for nucleotides, and the weighted comparison matrix of Gribskov and Burgess (1986). (2) a penalty of 3.0 for each gap and an additional 0.10 penalty for each symbol in each gap: and (3) no penalty for end gaps.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%: or about 91% to about 95%; or even about 96% to about 99%; of nucleotides that are identical or functionally equivalent to one or more of the nucleotide sequences provided herein are particularly contemplated to be useful in the practice of the disclosure.

Suitable standard hybridization conditions for the present disclosure include, for example, hybridization in 50% formamide, 5×Denhardt's solution, 5×SSC, 25 mM sodium phosphate, 0.1% SDS and 100 µg/mL of denatured salmon sperm DNA at 42° C. for 16 hr followed by 1 hr sequential washes with 0.1×SSC, 0.1% SDS solution at 60° C. to remove the desired amount of background signal. Lower stringency hybridization conditions for the present disclosure include, for example, hybridization in 35% formamide, 5×Denhardt's solution, 5×SSC, 25 mM sodium phosphate, 0.1% SDS and 100 µg/mL denatured salmon sperm DNA or E. coli DNA at 42° C. for 16 hr followed by sequential washes with 0.8×SSC, 0.1% SDS at 55° C. Those of ordinary skill in the art will recognize that conditions can be readily adjusted to obtain the desired level of stringency.

The present disclosure also encompasses nucleic acid segments that are complementary, essentially complementary, and/or substantially complementary to at least one or more of the specific nucleotide sequences specifically set forth herein. Nucleic acid sequences that are "complementary" are those that are capable of base pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to hp 51, from bp 3 to bp 52, from bp 4 to bp 53, and so forth.

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the disclosure to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present disclosure may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The term "therapeutically practical time period" means a time necessary for an active agent to be therapeutically effective. The term "therapeutically-effective" refers to a reduction in the severity and/or frequency of one or more symptoms, an elimination of symptoms, and/or one or more underlying causes, the prevention of an occurrence of one or more symptoms and/or their underlying cause, and/or an improvement or a remediation of damage.

A "therapeutic agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof. Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent. Cytokines may be also used as the therapeutic agent. Examples of such cytokines are lymphokines, monokines, and traditional polypeptide hormones. A cancer chemotherapy agent, such as docetaxel, may also be a therapeutic agent. For a more detailed description of anticancer agents and other therapeutic agents, those skilled in the art are referred to any number of instructive manuals including, but not limited to Hardman and Limbird (2001).

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the disclosure to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present disclosure may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder. As such, the terms "treatment," "treat," "treated," or "treating" may refer to therapy, or to the amelioration or the reduction, in the extent or severity of disease, of one or more symptom thereof, whether before or after its development afflicts a patient.

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Exemplary Cationic Liposomes

The use of cationic liposome nanoparticle delivery systems permit attachment of immunomodulatory compounds like toll-like receptor ligand(s) (TLR-L), interleukins, and such like to the particle surface and loading with both antigens and immune-stimulating agents (for example, in the form of proteins, peptides, small molecules. RNA. DNA, and the like), either free or encapsulated in nanoparticles. The inventors have demonstrated that the inclusion of immunomodulatory agents on the surface of, or within the body of the cationic nanoparticle liposomal formulations leads to engagement of TLR on immune cells, resulting in: 1) enhanced particle uptake by immune cells [i.e., antigen presenting cells (APC), such as dendritic cells]; 2) activation of immune cells (i.e., increased expression of co-stimulatory molecules, cytokine secretion, and surface MHC expression on APC); and 3) enhanced migration of immune cells to the lymph node for activation of an immune response.

Dendritic cells (DC) process and present antigens to T lymphocytes, inducing potent immune responses when encountered in association with activating signals, such as pathogen-associated molecular patterns. Using the 4T1 murine model of breast cancer, cationic liposomes containing monophosphoryl lipid A (MPL) and interleukin (IL)-12 were administered by intratumoral injection. The combination of the multivalent presentation of the Toll like receptor-4 ligand MPL and cytotoxic 1,2-dioleoyl-3-trmethylammonium-propane lipids induced cell death, decreased cellular proliferation, and increased serum levels of IL-1β and tumor necrosis factor (TNF)-α. Addition of recombinant IL-12 further suppressed tumor growth and increased expression of IL-1β, TNF-α, and interferon-γ. IL-12 also increased the percentage of cytolytic T cells, DC, and F4/80⁺ macrophages. While single agent therapy elevated levels of nitric oxide synthase 3-fold above basal levels in the tumor, combination therapy with MPL cationic liposomes and IL-12 stimulated a 7-fold increase, supporting the observed cell cycle arrest (loss of Ki-67 expression) and apoptosis (TUNEL positive). In mice bearing dual tumors, the growth of distal, untreated tumors mirrored that of liposome-treated tumors, supporting the presence of a systemic immune response.

Cationic liposomes may be formed from a single type of lipid, or a combination of two or more distinct lipids. For instance, one combination may include a cationic lipid and a neutral lipid, or a cationic lipid and a non-cationic lipid. Exemplary lipids for use in the cationic liposomes include but are not limited to DOTAP, DODAP, DDAB, DOTMA, MVL5, DPPC, DSPC, DOPE, DPOC, POPC, or any combination thereof. In one embodiment, the cationic liposome has one or more of the following lipids or precursors thereof:

N-[1-(2,3-dioleyloxy)propyl]-N,N,N-trimethylammonium chloride with a monovalent cationic head; N',N'-dioctadecyl-N-4,8-diaza-10-aminodecanoyl glycine amide; 1,4,7,10-tetraazacyclododecane cyclen; imidazolium-containing cationic lipid having different hydrophobic regions (e.g., cholesterol and diosgenin); 12-dioleoyl-sn-glycero-3-phosphoethanolamine (DOPE); 3β-[N—(N',N'-dimethyl-amino-ethane) carbamoyl] cholesterol (DC-Chol) and DOPE; O,O'-ditetradecanoyl-N-(α-trimethyl ammonio-acetyl) diethanol-amine chloride. DOPE and cholesterol, phosphatidylcholine; 1,2-dilinoleyl-4-(2-dimethylamino-ethyl)-[1,3]-dioxolane, 1,2-distearoyl-sn-glycerol-3-phosphocholine (DSPC) and cholesterol, 1-palmitoyl-2-oleoyl-sn-glycero-3-phosphocholine, DOPE, and 1,2-distearoyl-sn-glycero-3-phosphoethanolamine-N-(methoxy[polyethylene glycol-2000), 1,2-di-O-octadecenyl-3-trimethylammonium propane, cholesterol, and D-α-toco; 1,2-dioleoyl-3-trimethylammonium-propane, cholesterol; 3-β(N—(N',N'-dimethyl, N'-hydroxyethyl amino-propane) carbamoyl) cholesterol iodide, DMHAPC-Chol and DOPE in equimolar proportion, or 1-palmitoyl-2-oleoyl-sn-glycero-3-ethylphosphocholine:cholesterol, dimethyldioctadecylammonium (DDAB); 1,2-di-O-octadecenyl-3-trimethylarmnonium propane; N1-[2-((1S)-1-((3-aminopropyl)amino]-4-[di(3-amino-propyl)amino)amino]butylcarboxamido)ethyl-3,4-di[oleyloxy]-benzamide (MVL5); 1,2-dioleoyl-3-dimethylammonium-propane (DODAP); 1,2-di-O-octadecenyl-3-trimethylammonium propane (DOTMA); 1,2-dioleoyl-sn-glycero-3-phosphocholine (DOPC); 1-palmitoyl-2-oleoyl-sn-glycero-3-phosphocholine (POPC).

Chemotherapeutic Methods and Use

One aspect of the present disclosure concerns methods for using the disclosed cationic nanoparticle formulations for treating or ameliorating the symptoms of one or more forms of cancer. Such methods generally involve administering to a mammal (and in particular, to a human in need thereof), one or more of the disclosed cationic nanoparticle-based compositions, in an amount and for a time sufficient to treat (or, alternatively ameliorate one or more symptoms of) cancer in an affected mammal.

In certain embodiments, the cationic nanoparticle formulations described herein may be provided to the animal in a single treatment modality (either as a single administration, or alternatively, in multiple administrations over a period of from several hours (hrs) to several days or several weeks), as needed to treat the disease. Alternatively, in some embodiments, it may be desirable to continue the treatment, or to include it in combination with one or more additional modes of therapy, for a period of several weeks to several months or longer. In other embodiments, it may be desirable to provide the therapy in combination with one or more existing, or conventional, treatment regimens.

The present disclosure also provides for the use of one or more of the disclosed cationic nanoparticle compositions in the manufacture of a medicament for therapy and/or for the amelioration of one or more symptoms of cancer, and particularly for use in the manufacture of a medicament for treating and/or ameliorating one or more symptoms of a mammalian cancer.

The present disclosure also provides for the use of one or more of the disclosed cationic nanoparticle formulations in the manufacture of a medicament for the treatment of cancer, and in particular, the treatment of human cancers.

Therapeutic Kits

Commercially-packaged kits that included one or more of the disclosed cationic nanoparticle formulations along with instructions for using the nanoparticles in a particular treatment modality also represent another embodiment of the disclosure. Such kits may further optionally include one or more additional anti-cancer compounds, one or more diagnostic reagents, or one or more additional therapeutic compounds, pharmaceuticals, or such like.

The kits may be packaged for commercial distribution, and may further optionally include one or more delivery devices adapted to deliver the cationic nanoparticle composition(s) to an animal (e.g., syringes, injectables, and the like). Such kits typically include at least one vial, test tube, flask, bottle, syringe, or other container, into which the pharmaceutical composition(s) may be placed, and in one embodiment suitably aliquotted. Where a second pharmaceutical is also provided, the kit may also contain a second distinct container into which this second composition may be placed. Alternatively, a plurality of pharmaceutical compositions including the cationic nanoparticles disclosed herein may be prepared in a single mixture, such as a suspension or solution, and may be packaged in a single container, such as a vial, flask, syringe, catheter, cannula, bottle, or other suitable single container.

The kits of the present disclosure may also typically include a retention mechanism adapted to contain or retain the vial(s) or other container(s) in close confinement for commercial sale, such as, e.g., injection or blow-molded plastic containers into which the desired vial(s) or other container(s) may be retained to minimize or prevent breakage, exposure to sunlight, or other undesirable factors, or to permit ready use of the composition(s) included within the kit.

Pharmaceutical Formulations

In certain embodiments, the present disclosure concerns formulation of one or more cationic nanoparticle systems disclosed herein for administration to one or more cells or tissues of an animal, either alone, or in combination with one or more other modalities of diagnosis, prophylaxis, and/or therapy. The formulation of pharmaceutically acceptable excipients and carrier solutions is well known to those of ordinary skill in the art, as is the development of suitable dosing and treatment regimens for using the particular cationic nanoparticle compositions described herein in a variety of treatment regimens.

In certain circumstances it will be desirable to deliver the disclosed compositions in suitably-formulated pharmaceutical vehicles by one or more standard delivery methods, including, without limitation, subcutaneously, parenterally, intravenously, intramuscularly, intrathecally, orally, intraperitoneally, transdermally, topically, by oral or nasal inhalation, or by direct injection to one or more cells, tissues, or organs within or about the body of an animal.

The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, transdermal, subdermal, and/or intraperitoneal administration. In this regard, the compositions of the present disclosure may be formulated in one or more pharmaceutically acceptable vehicles, including for example sterile aqueous media, buffers, diluents, etc. For example, a given dosage of active ingredient(s) may be dissolved in a particular volume of an isotonic solution (e.g., an isotonic NaCl-based solution), and then injected at the proposed site of administration, or further diluted in a vehicle suitable for intravenous infusion (see, e.g., "REMINGTON'S PHARMACEUTICAL SCIENCES" 15$^{th}$ Ed., pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

Sterile injectable compositions may be prepared by incorporating the disclosed chemotherapeutic delivery system formulations in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The compositions disclosed herein may also be formulated in a neutral or salt form.

Pharmaceutically acceptable salts include the acid addition salts (formed with the free amino groups of the protein), and which are formed with inorganic acids such as, without limitation, hydrochloric or phosphoric acids, or organic acids such as, without limitation, acetic, oxalic, tartaric, mandelic, and the like. Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount, dosage regimen, formulation, and administration of chemotherapeutics disclosed herein will be within the purview of the ordinary-skilled artisan having benefit of the present teaching. It is likely, however, that the administration of a therapeutically-effective (i.e., a pharmaceutically-effective, chemotherapeutically-effective, or an anti-cancer-effective) amount of the disclosed compositions may be achieved by a single administration, such as, without limitation, a single injection of a sufficient quantity of the delivered agent to provide the desired benefit to the patient undergoing such a procedure. Alternatively, in other circumstances, it may be desirable to provide multiple, or successive administrations of the anti-cancer compositions disclosed herein, over relatively short or even relatively prolonged periods, as may be determined by the medical practitioner overseeing the administration of such compositions to the selected individual.

Typically, formulations of one or more of the compositions described herein will contain at least an effective amount of a first active agent. In one embodiment, the formulation may contain at least about 0.001% of each active ingredient, pat least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more, e.g., from about 0.2 to about 60 weight % or volume %, based upon the total formulation. Naturally, the amount of active compound(s) in each composition may be prepared in such a way that a suitable dosage will be obtained in any given unit dose of the compound. Factors such as solubility, bioavailability, biological $t_{1/2}$, route of administration, product shelf life, as well as other pharmacological considerations will be contemplated by one of ordinary skill in the art of preparing such pharmaceutical formulations, and as such, a variety of dosages and treatment regimens may be desirable.

Proper fluidity of the pharmaceutical formulations disclosed herein may be maintained, for example, by the use of a coating, such as e.g., a lecithin, by the maintenance of the required particle size in the case of dispersion, by the use of a surfactant, or any combination of these techniques. The inhibition or prevention of the action of microorganisms can be brought about by one or more antibacterial or antifungal agents, for example, without limitation, a paraben, chlorobutanol, phenol, sorbic acid, thimerosal, or the like. In many cases, an isotonic agent may be included, for example, without limitation, one or more sugars or sodium chloride, or any combination thereof. Prolonged absorption of the injectable compositions can be brought about by the use in the compositions of agents delaying absorption, for example without limitation, aluminum monostearate, gelatin, or a combination thereof.

While systemic administration is contemplated to be effective in many embodiments, it is also contemplated that formulations disclosed herein be suitable for direct injection into one or more organs, tissues, or cell types in the body. Administration of the disclosed compositions may be conducted using suitable means, including those known to the one of ordinary skill in the relevant medical arts.

The pharmaceutical formulations disclosed herein are not in any way limited to use only in humans, or even to primates, or mammals. In certain embodiments, the methods and compositions disclosed herein may be employed using avian, amphibian, reptilian, or other animal species. In some embodiments, however, the compositions of the present disclosure may be formulated for administration to a mammal, and in particular, to humans, as party of an oncology regimen for treating one or more cancers. The compositions disclosed herein may also be provided in formulations that are acceptable for veterinary administration, including, without limitation, to selected livestock, exotic or domesticated animals, companion animals (including pets and such like), non-human primates, as well as zoological or otherwise captive specimens, and such like.

Therapeutic Applications of Multi-Stage Delivery Systems

Nanotechnology is projected to fill the gap between significant scientific advances in the areas of cancer imaging and diagnosis, discovery and development of a plethora of anticancer drugs, and their translation into improvements in cancer management. With optimal anticancer treatment regimens still lacking, novel therapeutic approaches are being explored to supplement or replace traditional gold standards, including surgical resection (Finlayson et al., 2003) and radiation therapy (Elshaikh et al., 2005). While the curative potential of anticancer drugs is indisputable, limitations that hinder clinical translation and success include nonspecific drug delivery. In this section, various nanoparticles are described that have been successfully exploited for various therapeutic applications.

Liosomes

Liposomes represent a nanotherapeutic modality that shows immense clinical potential for drug delivery. These vesicular nanostructures, formed from phospholipid and cholesterol molecules, possess several advantages for drug delivery. First, their inner hydrophilic compartment can encapsulate water-soluble drugs, as well as therapeutic proteins. DNAs, and siRNAs. Second, with a diameter in the range of 100 nm, the drug payload can be substantial. Lastly, their functionalizaton with PEG can grant them with stealth-like properties, avoiding uptake by the RES. A PEGylated liposomal formulation, known as Doxil®, is currently in clinical trials for the treatment of Kaposi's sarcoma (Gabison, 2001). These stealth liposomes have long blood circulation times over non-PEGylated liposomes, and readily accumulate in tumors due to passive targeting (Kamaly et al., 2008; Zalipsky et al., 2007).

Another drug that was successfully encapsulated in liposomes is annamycin, a non-cross-resistant anthracycline (Booser et al., 2002). The pre-liposomal annamycin lyophilized powder contains phospholipids (dimyristoylphosphatidyl choline and dimyristoylphosphatidyl glycerol at a 7:3 molar ratio), annamycin (lipid:drug at a ratio 50:1 wt./wt.), and Tween-20. The surfactant in the formulation allows for better solubilization of the drug, shortening the reconstitution step, as well as a means to form nano-size carriers without destroying the liposomal structure (Zou et al., 1996). Similar to doxorubicin, the drug possesses native fluorescence in the red region. Flow cytometry data confirmed loading of annamycin liposomes into porous silicon microparticles. Loading resulted in a shift in the mean fluorescent intensity from 3 to 1285 AU. Other liposomal active agents that were successfully loaded into the multistage drug delivery system include paclitaxel, doxorubicin, and siRNA.

Polymer Micelles

Ringsdorf and coworkers worked in the early 1980s on the development of polymer micelles as drug delivery vehicles (Gros et al., 1981). These spherical, supramolecular constructs, with a size ranging from 10-100 nm, are formed from the self-assembly of biocompatible amphiphilic block copolymers in aqueous environments (Savic et al., 2003; Matsumura and Kataoka, 2009; Nakanishi et al., 2001). The hydrophilic outer portion, typically composed of PEG, forms a hydrating layer, while the hydrophobic core, composed of polymers such as poly(D,L-lactic acid) (PDLLA), poly($\varepsilon$-caprolactone) (PCL), and poly(propylene oxide) (PPO), houses the anticancer agent. The ability of the drug to be encapsulated within the hydrophobic core represents their main advantage, in addition to their innate possession of a PEG hydrophilic corona that prevents opsonization and RES uptake (Satomi et al., 2007), and their small size which leads to their preferential accumulation in tumor tissue through the EPR effect.

Currently, several polymeric micelle platforms are being explored in clinical trials. Kataoka and coworkers formulated doxorubicin-containing poly(ethylene glycol)-poly(L-aspartic acid) micelles (Nakanishi et al., 2001). This formulation, known as NK911, displayed long blood circulation times and nearly tripled the half-life of doxorubicin (Matsumura et al., 2004). Genexol-PM is another micelle formulation in clinical trials, and consists of PEG-PLA micelles that encapsulate paclitaxel. Findings showed that Genexol-PM was much more tolerable than the clinically used formulation of paclitaxel containing Cremephor® EL, a formulation that results in hypersensitivity reactions (Wiernik et al., 1987). As a result, the dose of paclitaxel administered to patients could be increased, which in turn resulted in enhanced anti-tumor efficacy in patients (Kim et al., 2004; Kim et al., 2004).

To further enhance selective delivery of chemotherapeutics to the lesion, doxorubicin and paclitaxel polymeric micelles have been loaded into the nanoporous matrix of the silicon microparticles. For doxorubicin the best loading was obtained with 1,2-distearoyl-phosphatidyl ethanolamine-methyl-poly(ethyleneglycol) anionic micelles loaded into oxidized porous silicon microparticles.

For promoting an understanding of the principles of the disclosure, reference will now be made to the embodiments, or examples, illustrated in the drawings and specific language is used to describe the same. It will, nevertheless be understood that no limitation of the scope is thereby intended. Any alterations and further modifications in the described embodiments, and any further applications of the principles of the disclosure as described herein are contemplated as would normally occur to one of ordinary skill in the art to which the disclosure relates.

The following example is included to demonstrate illustrative embodiments of the invention. It should be appreciated by those of ordinary skill in the art that the techniques disclosed in this example represents techniques discovered to function well. However, those of ordinary skill in the art should, in light of the present disclosure, appreciate that many changes can be made in the specific embodiments that are disclosed, and still obtain a like or similar result without departing from the spirit and scope of the invention.

Example 1

Materials

MPL from *Salmonella enteric* serotype Minnesota RE 595 and cholesterol (Sigma grade $\geq$99%) were purchased from Sigma-Aldrich (St. Louis, Mo., USA), 1,2-dipalmitoyl-sn-glycero-3-phosphocholine (DPPC) and 1,2-dioleoyl-3-trimethylammonium-propane (DOTAP) Chloride salt were obtained from Avanti Polar Lipids, Inc. (Alabaster, Ala., USA). Mouse Novex Cytokine Magnetic 10-Plex ELISA kits were purchased from Invitrogen (Grand Rapids, N.Y. USA). 4T1-luc2-td Tomato Bioware® Ultra Red mouse mammary cancer cells were purchased from Caliper Life Sciences (Hopkinton, Mass. USA). Recombinant mouse IL-12 was purchased from R&D Systems. Inc. (Minneapolis, Minn., USA).

Animals

BALB/c mice (4-6 wk old) were obtained from Charles River Laboratories, Inc. (Wilmington. Mass. USA). All procedures were performed in accordance with protocols reviewed and approved by the Institutional Animal Care and Use Committee at Houston Methodist Research Institute.

Preparation and Characterization of Liposomes

DOTAP liposomes were prepared using a molar ratio of 7:3:1 for DPPC: Cholesterol: DOTAP. Lipids (40 mg) were dissolved in a 3 mL Chloroform:Methanol (3:1) solution and 250 µg MPL, dissolved in chloroform at 5 mg/mL, was added. Organic solvent was removed by overnight heating at 55° C. in a Hei-Vap Series Heidolph Rotatory Evaporator (Schwabach, Germany). The liposomes were recovered in 2 mL PBS, followed by heating in a waterbath at 52° C. for 3 minutes, then vortexing for 3 minutes and sonication for 30 seconds. The heat, vortex and sonication cycle was repeated 3 times followed either by final sonication for 3 minutes to get the final liposome product or by extrusion through dual filters (200 nm), 8×, using a 10 mL Thermobarrel Extruder from Northern Lipids. Inc. (Burnaby, B.C., Canada). For liposomes containing cytokine, IL-12 was added to the hydrating PBS at a final concentration of 0.1 mg/mL. Adsorption of IL-12 to the liposomes was determined by quantitating the amount of IL-12 depleted from the solvent after removal of the liposomes by centrifugation using the BD™ Cytometric Bead Assay for mouse IL-12p70 (San Diego, Calif., USA). Size and charge of liposomes were characterized by Dynamic light scattering (DLS) and Zeta Potential analysis using a Malvern Zetasizer (Worcestershire, UK). Liposome size and shape were further characterized by Atomic Force Microscopy using a Bruker Multimode SPM system (Santa Barbara, Calif., USA). AFM images were acquired in PBS in contact mode using MLCT cantilevers purchased from Bruker with a spring constant at 0.01 N/m.

Cytotoxicity Studies

The cytotoxicity of cationic liposomes to 4T1 breast cancer cells was evaluated by flow cytometry using propodium iodide (PI). Using a 24 well plate format, cells were treated with 4 µg control or MPL liposomes, or free MPL (250 ng) for 24 hours. Cells were released using trypsin and treated with PI according to manufacturer's protocol (Invitrogen). Samples were analyzed using a LSR II™ Flow Cytometer (BD Biosciences, Mountain View, Calif., USA) equipped with FACSDIVA™ software (2007). In vivo tumor cytotoxicity of cationic liposomes was evaluated in BALB/c mice bearing 200 mm$^3$ 4T1 tumors 24 hours following intratumoral injection of liposomes (50 µL; 1 mg lipid). Excised tumors were embedded in paraffin, sectioned, and stained with hematoxylin and eosin or used for analysis of apoptosis using the DeadEnd™ Fluomometric TUNEL System (Promega, Madison, Wis., USA).

Multiplex Bead ELISA

Serum cytokines were analyzed 5 hours after intratumoral injection of liposomes using a mouse cytokine magnetic 10-plex panel kit (Invitrogen, Carlsbad, Calif., USA) for the Luminex® platform. Following retro-orbital eye bleed, plasma was collected by centrifugation at 1500 g for 10 minutes at 4° C. and stored at −80° C. Plates were prepared using 25 µL/well of the antibody-bound head. After 2 washes, 50 µL serum and 50 µL assay diluent (or 100 µL standard) were added and plates were incubated at room temperature for 2 hours on an orbital shaker. After two washes, 100 µL of biotinylated detector antibody was added to the heads and they were incubated for an additional hour, followed by two more washes and the addition of 100 µL streptavidin-RPE for 30 minutes. After a final two washes, beads were suspended in 125 µL wash solution and inserted into the XY platform of a Luminex MAGPIX Instrument (EMD Millipore, Billerica, Mass. USA). The assay protocol was designed using xPONENT software and samples were run at 100 events/bead region.

Immunhistochemistry

Tissues were quick frozen in OCT (Tissue-Tek) and stored at −80° C. Tissue sections (10 µm) were fixed with ice-cold acetone for 15 minutes at −20° C. and washed three times with IX PBS using trays followed by blocking with 5% fetal bovine serum in PBS. Fluorescence-labeled antibodies [e-flour 615 CD8 (clone 53-6.7; 1:50), e-flour 570 Ki-67 (clone solA15: 1:100; eBioscience, San Diego, Calif., USA); FITC F4/80 (MCA497A488; 1:100), Alexa Fluor 647 CD204 (MCA1322; 1:100, AbD Serotec, Raleigh N.C., USA); and 33D1 (1:100, BD Biosciences, San Jose. Calif.: 1:500 secondary anti-rat IgG Alexa Fluor® 546; Invitrogen) and iNOS (6/iNOS/NOS; 1:100 BD Biosciences, San Jose, Calif., USA; 1:500 anti-rabbit IgG-TRITC, Jackson Immunoresearch Labs, Inc. West Grove, Pa., USA)] were incubated with tissues overnight at 4° C. in the presence of 5% FBS. Slides were then washed three times with PBS and mounted with ProLong® Gold AntiFade with DAPI (Invitrogen). Images were taken using an A1 Nikon confocal microscope and the percent positive cells were determined by manual counting of four arbitrary regions in random samples.

Therapeutic Efficacy Studies

Breast cancer tumors were established in BALB/c mice by intramammary injection of 1×10$^5$ 4T1-luciferase cells. When tumors reached a median size of 100-200 mm$^3$, mice were administered intratumoral injections as follows: PBS control, Free MPL (6.25 µg), control liposomes (50 µL; 1 mg lipid); MPL liposomes (50 µL), and IL-12 (5 µg) with/without MPL liposomes. Tumor growth was monitored by caliper measurements three times per week and by luciferase expression measured weekly using the Xenogen IVIS-200 System (Perkin Elmer Inc., Waltham, Mass., USA) following intra-peritoneal injection of 75 mg/kg RediJect D-Luciferin (Perkin Elmer Inc.), 24-26 days after initiation of tumor growth, mice were sacrificed, blood was collected by retro-orbital bleeding, and tumor and spleen were collected for immunohistochemical, weight, and size analysis. Dual tumors were grown in naïve mice using the same experimental conditions with intratumoral injection of particles limited to a single tumor.

Results

Characterization of Cationic MPL Liposomes

In order to create localized necrosis for release of tumor antigens and uric acid, a cationic liposome embedded with the TLR-4 ligand MPL was created. MPL favors a Type 1 bias, supporting tumor regression, in immune responses. Dynamic light scattering supported an average diameter of 100.3±0.43 and 103.3±1.85 nm for control and MPL-loaded liposomes, with a poly dispersity index of 0.115±0.014 and 0.28±0.01, respectively. To evaluate the heterogeneity of the population, liposomes were bound to an oxidized silicon wafer, with 3D images of the wafers. The height image of the MPL liposomes supported a disperse population that was uniform in size. A line scan through the height image also supported homogeneity in size. The surface potential of the liposomes was approximately 47 mV for both control and MPL liposomes, supporting localization of MPL in the lipid bilayer. Addition of rIL-12 to the liposomes reduced the surface potential of the liposomes by 7 mV, supporting surface adhesion by rIL-12. Based on detection of unbound IL-12 using a Mouse IL-12p70 Enhanced Sensitivity Flex Set from BD Biosciences ($R^2$=0.987 for standard curve), 34% and 26% of cytokine was in bound state for control and MPL containing liposomes, respectively.

Evaluation of Liposome Cytotoxicity

To study particle cytotoxicity, 4T1 cells were cultured with 4 µg/mL liposomes for 24 hours and cell death was measured by flow cytometry based on propodium iodide (PI) uptake. Control and MPL liposomes induced cell death in 93% and 95% of the cells whereas control and free MPL treated cells displayed 14% and 16% cell death, respectively (n=3). Flow cytometry histograms of the FL2 orange-red channel show a shift in the entire population of liposome-treated cells.

The in vivo cytotoxicity of the cationic liposomes was studied in BALB/c 4T1 orthotopic tumors. When the tumor volumes reached 100-200 mm$^3$, intratumoral injections with PBS, free MPL, or liposomes were performed. After 24 hours, the mice were sacrificed and tumor tissue was analyzed by H&E and TUNEL staining. In contrast to control tumors, clear necrotic regions were visible in mice treated with MPL liposomes. Minimal cell death was present in control and MPL-treated liposomes based on TUNEL staining, while abundant cell death was present after treatment with both control and MPL liposomes.

Therapeutic Efficacy of Cationic Adjuvant Liposomes

To examine the impact of cationic MPL liposome on breast tumor growth, 4T1 orthotopic breast tumors were developed to a size of 100-200 mm$^3$ and intratumoral injections of liposomes were performed once a week for two weeks. Tumor growth was monitored by caliper measurements and luciferase expression using the IVIS Imaging System 200, and tumor weights were measured at the end of study. Despite inducing localized cell death, control cationic liposomes did not reduce the rate of tumor growth. However, addition of MPL to the liposomes led to a dramatic reduction in tumor growth. Similar to control liposomes, free MPL did not slow tumor growth. Bioluminescence imaging of luciferase expression following luciferin injection using the IVIS 200 imaging system supported the caliper data, with MPL liposome treatment blocking tumor progression. The mass of excised tumors on day 25 support a significant reduction in tumor growth following treatment of MPL liposomes compared to both PBS and control liposome treated mice.

Combination Adjuvant Therapy Increases Blockade of Tumor Growth

To create a microenvironment conducive to cell-mediated immunity the goal was to boost the immune response further by adding rIL-12 to the liposome cocktail. IL-12, produced by macrophages and dendritic cells, stimulates proliferation and activation of cytotoxic CD8$^+$ lymphocytes and NK cells, leading to the production of IFN-γ, and stimulating antigen-specific and nonspecific immune responses.

Figure 4:
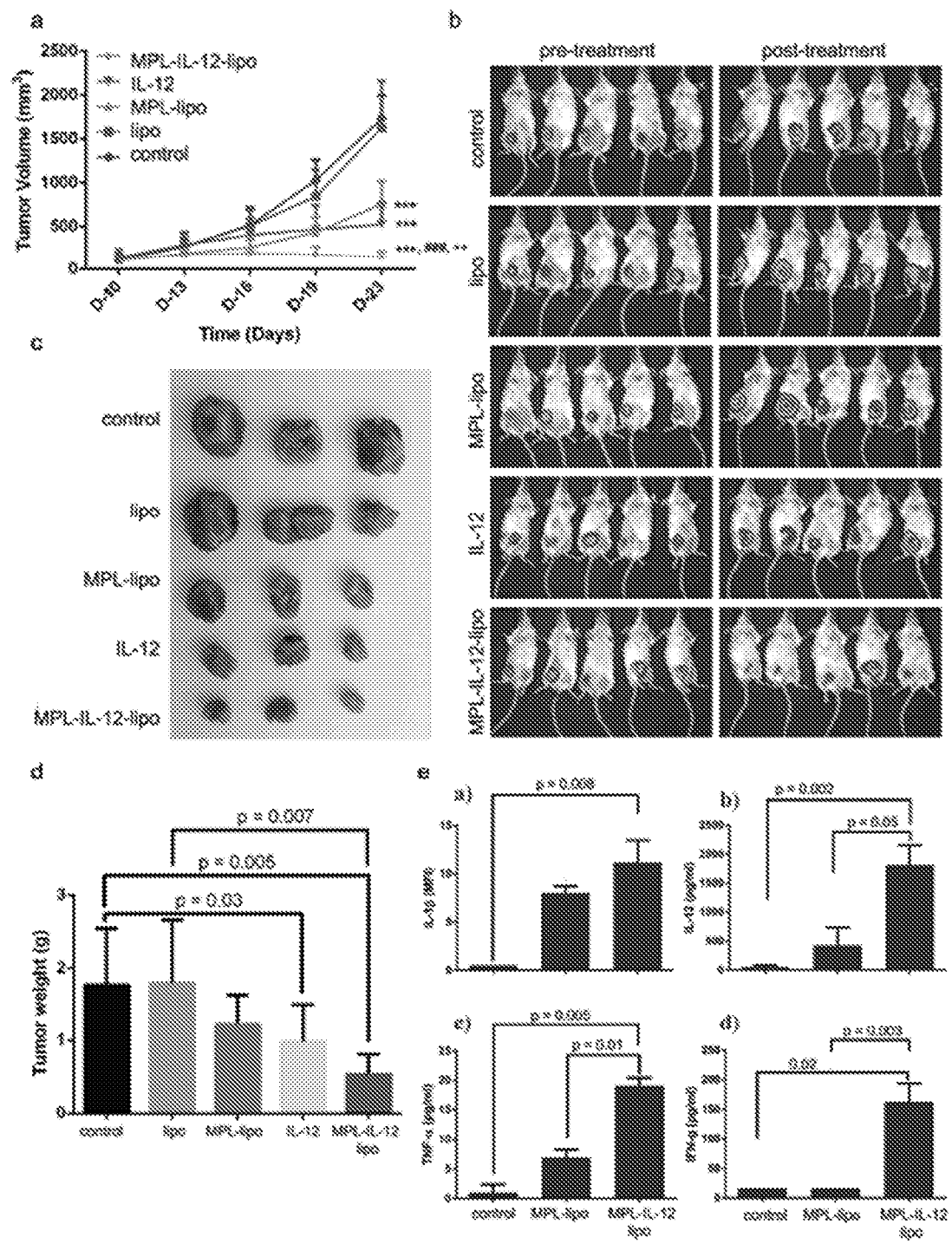

Combined therapy with liposomal MPL and IL-12 (5 μg) was superior to either agent delivered independently with respect to inhibiting tumor growth. While control liposome treated tumors were similar in size to tumors in untreated animals, those treated with combination adjuvant were unchanged from the start of treatment based on caliper measurements (n=5/group) and were undetectable in some animals by bioluminescence (FIG. 4B). An image was created of three randomly selected tumors from each group with the mean tumor weight and standard deviation of all animals in each group. Serum cytokine measurements following single or combination therapy supported increases in IL-1, IL-12 and TNF-α by all adjuvant therapy, with a significant enhancement by combination over single agent therapy. Only mice treated with IL-12 had an increase in serum IFN-γ.

Changes in the Cellular Phenotype of the Tumor Microenvironment

To study phenotypic changes and impact on cell growth in the tumor microenvironment following treatment with adjuvant particles, we analyzed tissues section by immunofluorescence. Cellular proliferation, based on Ki-67 expression, was similar for control and liposome treated animals (40%). However, addition of MPL to the liposomes or injection with rIL-12 or MPL-IL-12-liposomes blocked proliferation (5-10%). The presence of CD8+ T cells in the tumor was negligible in control and liposomes-treated mice (0.8%), as were F4/80 (7%) and iNOS (8%) expressing macrophages. Treatment with MPL-IL-12-liposomes led to significant increases in each of these populations (28%, 36%, 54% for CD8+ T cells, F4/80 and iNOS macrophages), as well as in 33D1+ dendritic cells. The percentage of CD204 macrophages were not significantly altered in the tumors of mice treated with adjuvant liposomes. In conclusion, MPL-IL-12-liposomes augment infiltration of cytotoxic T cells and immune potentiating immune cells, and reduce proliferation of cells within the tumor.

Single Tumor Therapy in the Presence of Dual Tumors

MPL-IL-12-liposome therapy was administered to mice by intratumoral injection to induce cell death, block proliferation, and stimulate a cytokine and cellular milieu conducive to anti-cancer immunity. Since the presence of pro-inflammatory cytokines increased in the serum of treated mice, we wanted to test for the presence of systemic anti-cancer immunity. Growth of distal tumors in mice receiving single tumor therapy was evaluated by caliper measurements of tumor volume, tumor weight and bioluminescence based on luciferase expression in cancer cells. For all groups, growth of the distal tumor mirrored that to the treated tumor, with MPL-IL-12-liposome therapy inhibiting growth of the tumor.

Discussion

While the addition of MPL to cationic liposomes did not alter the surface potential of the nanoparticles, addition of IL-12 caused a 7 mV reduction in the zeta potential, supporting surface presentation of the cytokine. The advantage of nanoparticle-based presentation of IL-12 is reduction in serum levels, avoiding exposure to cytotoxic levels and permitting a more sustained, localized release (Simpson-Abelson et al., 2009). The efficacy of using liposomal nanocarriers to reduce drug toxicity while enhancing immunity has also been demonstrated for other agents, such as amphotericin B in the fight against murine leishmaniasis (Daftarlan et al., 2013).

While both control and MPL liposomes were toxic to cancer cells as anticipated, injection of MPL liposomes, unlike control liposomes, reduced cellular proliferation in tumors. The decrease in proliferation may be attributed to increases in enzymes, such as iNOS which was significantly upregulated in tumors following injection with MPL-liposomes. Activation of APC with pathogens or pathogen-specific molecules (e.g., MPL) activates pathogen recognition receptors (PRRs), leading to release of effector molecules such as nitric oxide (NO) synthase (iNOS). NO has been shown to favor cell cycle arrest, mitochondria respiration, senescence or apoptosis (Napoli et al., 2013). While resting immune cells lack expression of iNOS enzyme, TLR engagement with CD14-LPS (or MPL) complex activates intracellular signaling, which includes IRAK and MyD88 adaptors, leading to iNOS transcription (Lowenstein and Pabelko, 2004). Herein it was demonstrated that MPL liposomes and IL-12 induce small increases in iNOS expression (3-fold), while combination therapy with IL-12 and MPL liposomes synergistically increase iNOS expression (7-fold).

In addition to releasing tumor antigen complexes, dying cancer cells release uric acid and lysosomal enzymes. These cellular components, as well as MPL, activate the Nod-like receptor protein 3 (NLRP3) inflammasome (Martinon et al., 2006; Hornung et al., 2008). While NLRP3 activation has been linked to infiltration by DC and macrophages, we did not see significant increases in either 33D$^+$ DC or F4/8$^+$ macrophages following treatment with MPL-liposomes. However, when IL-12 was introduced into the liposomal formulation there were large increases in DC. F4/80$^+$ macrophages and CD8$^+$ T cells. NLRP3 activation stimulates secretion of IL-1β and IL-18 (Dinarello, 2006). We previously demonstrated that porous silicon particle-based presentation of MPL in mice hearing 4T1 tumors augments its ability to increase serum IL-1β levels, as well as other pro-inflammatory cytokines including IL-12, TNF-α and IFN-γ (Meraz et al., 2012). In this study, MPL liposomes similarly increased serum levels of IL-1β, IL-12, and TNF-α. Addition of IL-12 lead to significantly greater increases in each of these cytokines and stimulated production of INF-γ.

Cytokines patterns elicited by activated T cells favor either cell-mediated immunity (i.e., T helper (Th)-1 biased), characterized by IFN-γ, IL-2 and TNF-α, or humoral immunity (Th-2 biased), characterized by secretion of IL-4, IL-5, IL-6 and IL-10. IL-12 has potent anti-tumor effects and has been shown to direct immune reactions from Th-2 to Th-1 (Manetti et al., 1993; Sypek et al., 1993). As stated, IL-12 enhanced production of Th-1 cytokines and increased cytolytic T cells, DC and F4/80$^+$ macrophages, as well as enhancing production of iNOS. Inratumoral administration of combination IL-12 and MPL liposomes completely blocked 4T1 tumor growth. Combination liposomal therapy was able to induce similar reductions in tumor growth in both treated and distal tumors, suggesting a systemic immune response. Future studies will seek to differentiate specific anti-tumor immune responses from those resulting from general immune activation (e.g., cancer cell death due to TNF-α), and will seek to optimize particle-based accumulation of cytokines in the tumor, with an emphasis on studying dose effects and controlled, sustained presentation of cytokines for an optimal anti-cancer response with minimal cytotoxicity.

Example 2

Adjuvant Cationic Liposomes Presenting MPL and IL-12

This example describes the elicitation of cancer-specific de novo host immune responses through injection of tumors with cationic adjuvant liposomes. The in vivo immunomodulatory properties of liposomes containing MPL and recombinant IL-12 (rIL-12) were examined using an immune competent 4T1 mouse model of breast cancer. The impact of adjuvant liposomes on cell viability and tumor growth was examined, as was the impact of the particles on the cytokine milieu and immune cell phenotype of the tumor.

Dendritic cells (DC) process and present antigens to T lymphocytes, inducing potent immune responses when encountered in association with activating signals, such as pathogen-associated molecular patterns. Using the 4T1 murine model of breast cancer, cationic liposomes containing monophosphoryl lipid A (MPL) and interleukin (IL)-12 were administered by intratumoral injection. Combination multivalent presentation of the Toll like receptor-4 ligand, MPL, and cytotoxic 1,2-dioleoyl-3-trimethylammonium-propane lipids induced cell death, decreased cellular proliferation, and increased serum levels of IL-1 J and tumor necrosis factor (TNF)-α. Addition of recombinant IL-12 further suppressed tumor growth and increased expression of IL-1β, TNF-α, and interferon-γ, IL-12 also increased the percentage of cytolytic T cells, DC, and F4/80$^+$ macrophages. While single agent therapy elevated levels of nitric oxide synthase 3-fold above basal levels in the tumor, combination therapy with MPL cationic liposomes and IL-12 stimulated a 7-fold increase, supporting the observed cell cycle arrest (loss of Ki-67 expression) and apoptosis (TUNEL-positive). In mice bearing dual tumors, the growth of distal, untreated tumors mirrored that of liposome-treated tumors, supporting the presence of a systemic immune response.

Experimental Details

Materials.

MPL from *Salmonella enteric* serotype Minnesota RE 595 and cholesterol (Sigma grade ≥99%) were purchased from Sigma-Aldrich (St. Louis, Mo., USA). 1,2-dipalmitoyl-sn-glycero-3-phosphocholine (DPPC) and 1,2-dioleoyl-3-tri-methylammnonium-propane (DOTAP) chloride salt were obtained from Avanti Polar Lipids, Inc. (Alabaster, Ala., USA). Mouse Novex Cytokine Magnetic 10-Plex ELISA kits were purchased from Invitrogen (Grand Rapids, N.Y., USA). 4T1-luc2-td Tomato Bioware® Ultra Red mouse mammary cancer cells were purchased from Caliper Life Sciences (Hopkinton. Mass. USA). Recombinant mouse IL-12 was purchased from R&D Systems. Inc. (Minneapolis, Minn., USA).

Animals.

BALB/c mice (4 to 6-wks' old) were obtained from Charles River Laboratories, Inc. (Wilmington. Mass. USA). All procedures were performed in accordance with protocols reviewed and approved by all required institutional animal care and use committees.

Preparation and Characterization of Liposomes.

DOTAP liposomes were prepared using a molar ratio of 7:3:1 for DPPC:Cholesterol:DOTAP. Lipids (40 mg) were dissolved in a 3-mL chloroform:methanol (3:1) solution, and 250 µg MPL (dissolved in chloroform at 5 mg/mL) was added. Organic solvent was removed by overnight heating at 55° C. in a Hei-Vap® series Heidolph rotatory evaporator (Schwabach, Germany). The liposomes were recovered in 2 mL PBS, followed by heating in a water bath at 52° C. for 3 min, then vortexing for 3 min, and sonication for 30 sec. The heat-vortex-sonication cycle was repeated 3 times, followed either by final sonication for 3 min to get the final liposome product, or by extrusion through dual filters (200 nm), 8×, using a 10-mL LIPEX® Thermobarrel Extruder from Northern Lipids. Inc. (Burnaby, BC. Canada). For liposomes containing cytokine, IL-12 was added to the hydrating PBS at a final concentration of 0.1 mg/mL. Adsorption of IL-12 to the liposomes was determined by quantitating the amount of IL-12 depleted from the solvent after removal of the liposomes by centrifugation using the BD™ Cytometric Bead Assay for mouse IL-12p70 (San Diego, Calif. USA). Size and charge of liposomes were characterized by Dynamic light scattering (DLS) and Zeta Potential analysis using a Zetasizer® (Malvern Instruments, Worcestershire. UK). Liposome size and shape were further characterized by Atomic Force Microscopy using a MultiMode 8® SPM system (Bruker Corp., Santa Barbara, Calif. USA). AFM images were acquired in PBS in contact mode using MLCT cantilevers with a spring constant at 0.01 N/m (Bruker).

Cylotoxicity Studies.

The cytotoxicity of cationic liposomes to 4T1 breast cancer cells was evaluated by flow cytometry using propidium iodide (PI). Using a 24-well plate format, cells were treated with 4 µg control or MPL liposomes, or free MPL (250 ng) for 24 hr. Cells were released using trypsin and treated with PI according to manufacturer's protocol (Invitrogen). Samples were analyzed using a LSR II® Flow Cytometer (BD Biosciences. Mountain View, Calif., USA) equipped with FACSDIVA™ software (2007). In vivo tumor cytotoxicity of cationic liposomes was evaluated in BALB/c mice bearing 200 mm$^3$ 4T1 tumors 24 hr following intratumoral injection of liposomes (50 µL; 1 mg lipid). Excised tumors were embedded in paraffin, sectioned, and stained with hematoxylin/eosin, or analyzed for apoptosis using the DeadEnd® Fluorometric TUNEL System (Promega Corp., Madison. Wis., USA).

Multiplex Bead ELISA. Serum cytokines were analyzed 5 hr after intratumoral injection of liposomes using a mouse cytokine magnetic 10-plex panel kit (Invitrogen, Carlsbad, Calif. USA) for the Luminex® platform. Following retro-orbital eye bleed, plasma was collected by centrifugation at 1500×g for 10 min at 4° C. and stored at −80° C. Plates were prepared using 25 μL/well of the antibody-bound bead. After 2 washes, 50 μL serum and 50 μL assay diluent (or 100 μL standard) were added and plates were incubated at room temperature for 2 hr on an orbital shaker. After two washes, 100 μL of biotinylated detector antibody was added to the beads and they were incubated for an additional hr, followed by two more washes and the addition of 100 μL streptavidin-RPE for 30 min. After a final two washes, beads were suspended in 125 μL wash solution and inserted into the XY platform of a Luminex® MAGPIX Instrument (EMD Millipore, Billerica, Mass., USA). The assay protocol was designed using xPONENT software and samples were run at 100 events/bead region.

Immunohistochemistry.

Tissues were quick frozen in OCT (Tissue-Tek) and stored at −80° C. Tissue sections (10 μm) were fixed with ice-cold acetone for 15 min at −20° C. and washed three times with 1×PBS using trays followed by blocking with 5% fetal bovine serum in PBS. Fluorescently-labeled antibodies [eFluor® 615 CD8 (clone 53-6.7; 1:50), eFluor® 570 Ki-67 (clone solA15; 1:100; eBioscience, San Diego, Calif. USA); FITC F4/80 (MCA497A488; 1:100), Alexa-Fluor® 647 CD204 (MCA1322; 1:100, AbD Serotec, Raleigh N.C. USA); and 33D1 (1:100, BD Biosciences, San Jose, Calif.; 1:500 secondary anti-rat IgG Alexa-Fluor® 546: Invitrogen) and iNOS (6/iNOS/NOS; 1:100 BD Biosciences. San Jose. Calif., USA; 1:500 anti-rabbit IgG-TRITC. Jackson ImmunoResearch Laboratories. Inc., West Grove, Pa. USA)] were incubated with tissues overnight at 4° C. in the presence of 5% FBS. Slides were then washed three times with PBS and mounted with ProLong® Gold AntiFade® with DAPI (Invitrogen). Images were obtained using a confocal microscope (A1 Nikon), and the percent-positive cells were determined by manual counting of four arbitrary regions in random samples.

Therapeutic Efficacy Studies.

Breast cancer tumors were established in BALB/c mice by intramammary injection of $1\times10^5$ 4T1-luciferase cells. When tumors reached a median size of 100-200 mm³, mice were administered intratumoral injections as follows: PBS control. Free MPL (6.25 μg), control liposomes (50 μL; 1 mg lipid): MPL liposomes (50 μL), and IL-12 (5 μg) with/without MPL liposomes. Tumor growth was monitored by caliper measurements three times per week and by luciferase expression measured weekly using the Xenogen IVIS® Imaging System 200 Series (Perkin-Elmer. Inc., Waltham, Mass., USA) following intra-peritoneal injection of 75 mg/kg RediJect® D-Luciferin (Perkin Elmer, Inc.), 24 to 26 days after initiation of tumor growth, mice were sacrificed, blood was collected by retro-orbital bleeding, and tumor and spleen were collected for immunohistochemical, weight, and size analysis. Dual tumors were grown in naïve mice using the same experimental conditions with intratumoral injection of particles limited to a single tumor.

Results

Characterization of Cationic MPL Liposomes.

Figure 1:
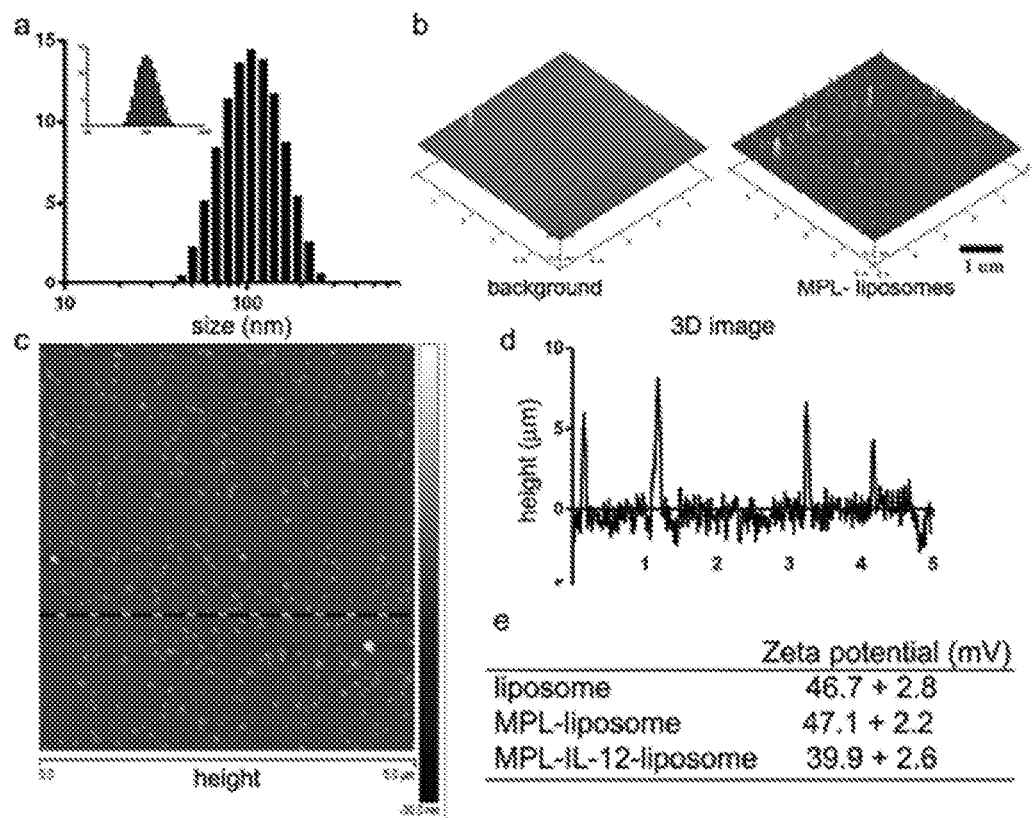
FIGS. 1A-E. Characterization of liposomes. A) Dynamic light scattering was used to assess particle size. The size distribution of MPL-liposomes is shown, with the inset showing the size distribution of control liposomes. B) 3D atomic force microscopy images show the surface topography of an oxidized silicon chip before and after binding of MPL-liposomes. C) 2D height images showing a homogeneous population of MPL liposomes. The height of particles lying on the line is displayed in the spectra in 'D'. E) Zeta potential of each liposome population.

In order to create localized necrosis for release of tumor antigens and uric acid, a cationic liposome embedded with the TLR-4 ligand MPL was created. MPL favors a Type 1 bias, supporting tumor regression, in immune responses. Dynamic light scattering (FIG. 1A) supported an average diameter of 100.3±0.43 and 103.3±1.85 nm for control and MPL-loaded liposomes, with a poly-dispersity index of 0.115±0.014 and 0.28±0.01, respectively. To evaluate the heterogeneity of the population, liposomes were bound to an oxidized silicon wafer, with 3D images of the wafers display in FIG. 1B. The height image of the MPL liposomes (FIG. 1C) supported a disperse population that was uniform in size. A line scan through the height image also supported homogeneity in size (FIG. 1D). The surface potential of the liposomes was approximately 47 mV for both control and MPL liposomes, supporting localization of MPL in the lipid bilayer (FIG. 1E). Addition of rIL-12 to the liposomes reduced the surface potential of the liposomes by 7 mV, supporting surface adhesion by rIL-12. Based on detection of unbound IL-12 using a Mouse IL-12p70 Enhanced Sensitivity Flex Set from BD Biosciences ($R^2=0.987$ for standard curve), 34% and 26% of cytokine was in bound state for control and MPL containing liposomes, respectively.

Evaluation of Liposome Cytotoxicity.

Figure 2:
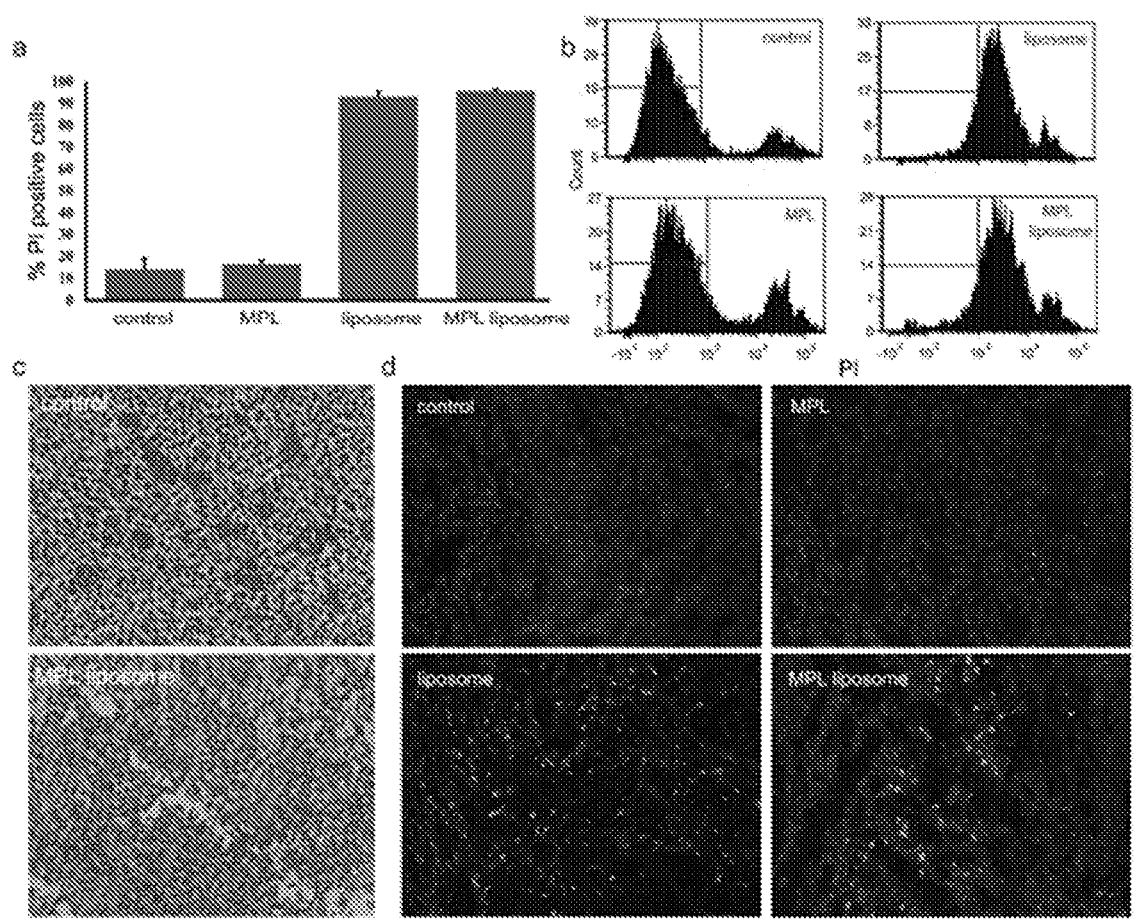
FIGS. 2A-D. Cytotoxic nature of cationic liposomes. A) Cell death as measured by propidium iodide uptake in 4T1 cells following a 24 hr incubation with 2 µg/ml DOTAP liposomes or 1 µg/ml MPL. B) Flow cytometry histograms illustrate the impact of MPL and/or liposomes on cell viability. C) H&E staining of BALB/c 4T1 tumor sections following treatment with MPL liposomes. D) TUNEL staining of tumor sections following treatment of mice bearing 4T1 tumors with MPL or liposomes.

To study particle cytotoxicity, 4T1 cells were cultured with 4 μg/mL liposomes for 24 hr and cell death was measured by flow cytometry based on propidium iodide (PI) uptake. Control and MPL liposomes induced cell death in 93% and 95% of the cells, whereas control and free MPL treated cells displayed 14% and 16% cell death, respectively (n=3; FIG. 2A). Flow cytometry histograms of the FL2 orange-red channel show a shift in the entire population of liposome-treated cells (FIG. 2B).

The in vivo cytotoxicity of the cationic liposomes was studied in BALB/c 4T1 orthotopic tumors. When the tumor volumes reached 100-200 mm³, intratumoral injections with PBS, free MPL, or liposomes were performed. After 24 hr, the mice were sacrificed and tumor tissue was analyzed by H&E and TUNEL staining. In contrast to control tumors, clear necrotic regions were visible in mice treated with MPL liposomes (FIG. 2C). Minimal cell death was present in control and MPL-treated liposomes based on TUNEL staining, while abundant cell death was present after treatment with both control and MPL liposomes (FIG. 2D).

Therapeutic Efficacy of Cationic Adjuvant Liposomes.

Figure 3:
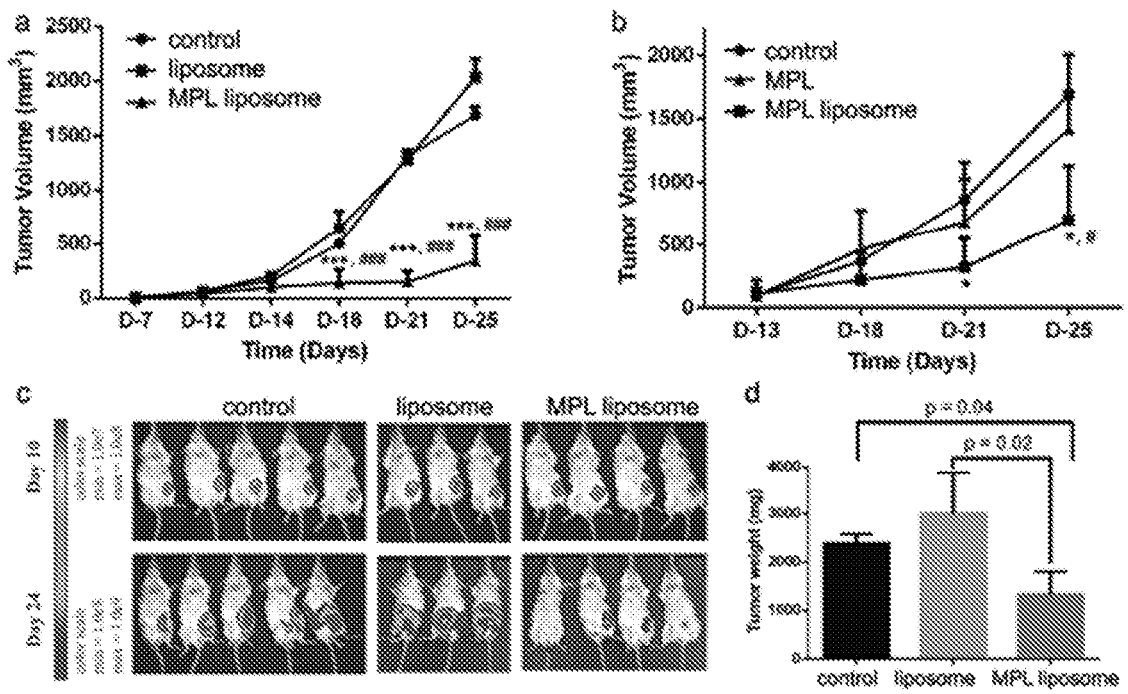

To examine the impact of cationic MPL liposome on breast tumor growth, 4T1 orthotopic breast tumors were developed to a size of 100-200 mm³, and intratumoral injections of liposomes were performed once a week for two weeks. Tumor growth was monitored by caliper measurements and luciferase expression using the Xenogen IVIS® Imaging System 200, and tumor weights were measured at the end of study. Despite inducing localized cell death, control cationic liposomes did not reduce the rate of tumor growth (FIG. 3A). However, addition of MPL to the liposomes led to a dramatic reduction in tumor growth. Similar to control liposomes, free MPL did not slow tumor growth (FIG. 3B). Bioluminescence imaging of luciferase expression following luciferin injection using the Senogen IVIS® Imaging System 200 supported the caliper data, with MPL liposome treatment blocking tumor progression (FIG. 3C). The mass of excised tumors on day 25 support a significant reduction in tumor growth following treatment of MPL liposomes compared to both PBS and control liposome treated mice (FIG. 3D).

Combination Adjuvant Therapy Increases Blockade of Tumor Growth.

To create a microenvironment conducive to cell-mediated immunity our goal was to boost the immune response further by adding rIL-12 to the liposome cocktail. IL-12, produced by macrophages and dendritic cells, stimulates proliferation and activation of cytotoxic $CD8^+$ lymphocytes and NK cells, leading to the production of IFN-γ, and stimulating antigen-specific and nonspecific immune responses.

Combined therapy with liposomal MPL and IL-12 (5 µg) was superior to either agent delivered independently with respect to inhibiting tumor growth. While control liposome treated tumors were similar in size to tumors in untreated animals, those treated with combination adjuvant were unchanged from the start of treatment based on caliper measurements (FIG. 4A, n=5/group) and were undetectable in some animals by bioluminescence (FIG. 4B). An image of three randomly selected tumors from each group is presented in FIG. 4C with the mean tumor weight and standard deviation of all animals in each group presented in FIG. 4D. Serum cytokine measurements following single or combination therapy supported increases in IL-1β, IL-12, and TNF-α by all adjuvant therapy, with a significant enhancement by combination over single agent therapy (FIG. 4E). Only mice treated with IL-12 had an increase in serum IFN-γ.

Changes in the Cellular Phenotype of the Tumor Microenvironment.

To study phenotypic changes, and the impact on cell growth in the tumor microenvironment following treatment with adjuvant particles, tissue sections were examined by immunofluorescence (FIG. 5A and FIG. 5B). Cellular proliferation, based on Ki-67 expression, was similar for control and liposome treated animals (40%). However, addition of MPL to the liposomes or injection with rIL-12 or MPL-IL-12-liposomes blocked proliferation (5-10%). The presence of CD8+ T cells in the tumor was negligible in control and liposomes-treated mice (0.8%), as were F4/80 (7%) and iNOS (8%) expressing macrophages. Treatment with MPL-IL-12-liposomes led to significant increases in each of these populations (28%, 36%, 54% for CD8+ T cells. F4/80 and iNOS macrophages), as well as in 33D1+ dendritic cells. The percentage of CD204 macrophages were not significantly altered in the tumors of mice treated with adjuvant liposomes. In conclusion. MPL-IL-12-liposomes augment infiltration of cytotoxic T cells and immune potentiating immune cells, and reduce proliferation of cells within the tumor.

Single Tumor Therapy in the Presence of Dual Tumors.

MPL-IL-12-liposome therapy was administered to mice by intratumoral injection to induce cell death, block proliferation, and stimulate a cytokine and cellular milieu conducive to anti-cancer immunity. Since the presence of proinflammatory cytokines increased in the serum of treated mice, the presence of systemic anti-cancer immunity was then assessed. Growth of distal tumors in mice receiving single tumor therapy was evaluated by caliper measurements of tumor volume (FIG. 6A), tumor weight (FIG. 6B), and bioluminescence (FIG. 6C), based on luciferase expression in cancer cells. For all groups, growth of the distal tumor mirrored that to the treated tumor, with MPL-IL-12-liposome therapy inhibiting growth of the tumor.

Discussion

While the addition of MPL to cationic liposomes did not alter the surface potential of the nanoparticles, addition of IL-12 caused a 7-mV reduction in the zeta potential, supporting surface presentation of the cytokine. The advantage of nanoparticle-based presentation of IL-12 was reduction in serum levels, thus avoiding exposure to cytotoxic levels, and permitting a more sustained, localized release (Simpson-Abelson et al., 2009). The efficacy of using liposomal nanocarriers to reduce drug toxicity, while enhancing immunity, has also been demonstrated for other agents, such as amphotericin B in the fight against murine leishmaniasis (Daftarian et al., 2013).

While both control and MPL liposomes were toxic to cancer cells as anticipated, injection of MPL liposomes, unlike control liposomes, reduced cellular proliferation in tumors. The decrease in proliferation may be attributed to increases in enzymes, such as iNOS, which was significantly upregulated in tumors following injection with MPL-liposomes. Activation of APC with pathogens or pathogen-specific molecules (e.g., MPL) activates pathogen recognition receptors (PRRs), leading to release of effector molecules such as nitric oxide (NO) synthase (iNOS). NO has been shown to favor cell cycle arrest, mitochondria respiration, senescence or apoptosis (Napoli et al., 2013). While resting immune cells lack expression of iNOS enzyme, TLR engagement with CD14-LPS (or MPL) complex activates intracellular signaling, which includes IRAK and MyD88 adaptors, leading to iNOS transcription (Lowenstein, and Padalko, 2004). In the present study, it was shown that MPL liposomes and IL-12 induced small increases in iNOS expression (3-fold), while combination therapy with IL-12 and MPL liposomes synergistically increased iNOS expression (7-fold).

In addition to releasing tumor antigen complexes, dying cancer cells release uric acid and lysosomal enzymes. These cellular components, as well as MPL, activate the Nod-like receptor protein 3 (NLRP3) inflammasome (Martinon et al., 2006; Hornung et al., 2008). While NLRP3 activation has been linked to infiltration by DC and macrophages, no significant increases were observed in either 33D1 DC or F4/80+ macrophages following treatment with MPL-liposomes. However, when IL-12 was introduced into the liposomal formulation there were large increases in DC. F4/80+ macrophages and CD8 T cells. NLRP3 activation stimulates secretion of IL-1β and IL-18 (Dinarello, 2006).

It was previously demonstrated that porous silicon particle-based presentation of MPL in mice bearing 4T1 tumors augments its ability to increase serum IL-1β levels, as well as other pro-inflammatory cytokines including IL-12, TNF-α and IFN-γ (Meraz et al., 2012). In this study. MPL liposomes similarly increased serum levels of IL-1β, IL-12, and TNF-α. Addition of IL-12 led to a significantly greater increase in each of these cytokines, and stimulated the production of INF-γ.

Cytokines patterns elicited by activated T cells favor either cell-mediated immunity (i.e. T helper (Th)-1 biased), characterized by IFN-γ, IL-2 and TNF-α, or humoral immunity (Th-2 biased), characterized by secretion of IL-4, IL-5, IL-6 and IL-10. IL-12 has potent anti-tumor effects and has been shown to direct immune reactions from Th-2 to Th-1 (Manetti et al., 1993; Sypek et al., 1993). As stated, IL-12 enhanced production of Th-1 cytokines and increased cytolytic T cells, DC and F4/80+ macrophages, as well as enhancing production of iNOS. Intratumoral administration of a combination of IL-12 and MPL liposomes completely blocked 4T1 tumor growth. Combination liposomal therapy was able to induce similar reductions in tumor growth in both treated and distal tumors, suggesting a systemic immune response.

Example 3

Chronic inflammation contributes to immune suppression within the tumor microenvironment through a multitude of physiological changes, including up-regulation of checkpoint inhibitors and alterations in the phenotype and responsiveness of tissue immunocytes.

In Vivo and Ex Vivo Tumor Imaging.

Preliminary data was acquired using the orthotopic 4T1 murine model. Intravital confocal imaging of a Tomato Bioware® Ultra Red tumor and FITC dextran-filled vasculature revealed a large network of vessels at the tumor periphery (FIG. 7A). CT imaging analysis of a tumor after perfusion with microfil revealed that macrovasculature is mostly localized at the tumor periphery (FIG. 7B). CT data were acquired on an Explore Locus SP (RS) pre-clinical Specimen Scanner (GE Medical Systems. London Ontario), a specimen-dedicated cone-beam volume CT system with a tungsten source X-ray tube. During imaging, objects were rotated in 1.0-degree increments (360 views) on a holder between the X-Ray source and a CCD-based detector. The density and location of microvasculature in tumor sections was defined by IHC (FIGS. 7C and D). Excised tumors were fixed, embedded in paraffin, sectioned, and stained with anti-CD31 antibody. Images were acquired from labeled sections with the ImageXpress® Micro XL (Molecular Devices, Sunnyvale. Calif., USA) optical imaging system equipped with RGB filters and a 10× objective. Micrographs were stitched together and masks created to enable us to quantitate vessels located in concentric rings across the tumor.

Tracking Inflammation with MRI.

Macrophage accumulation has been documented to contribute to cancer progression through suppression of the immune response and promotion of tumor vascularization (Mielgo et al., 2013). V-sense is a perfluorocarbon emulsion that is taken up by monocytes and macrophages, allowing for in-vivo detection through $^{19}F$ MRI. Ahrens, et al. (2011) successfully quantified V-sense in inflamed tissues of the central nervous system in an ex-vivo model of allergic encephalomyelitis, which they correlated with immunohistochemistry to confirm co-localization of V-sense emulsion droplets and macrophages. Hitchens et al. (2011) detected perfluorocarbon-labeled macrophages in a model of cardiac allograft rejection, which was confirmed via immunohistochemistry and histology. V-sense was used to study the impact of IL-12 on macrophage infiltration into the tumor (FIG. 8). In vitro, V-sense was taken up by RAW macrophages and $^{19}F$ MRI revealed a positive correlation between cell number and signal intensity (FIG. 8A). Confocal images in FIG. 8B show V-sense (red) uptake by Celltracker™ Green RAW cells. Merging of proton and fluorine images revealed differences in tumor distribution 24 hours post IL-12 intratumoral injection, when compared with sham control animals (FIG. 8C). Confocal micrographs of tumors extracted 24 hours post imaging supported strong penetration of V-sense signal into tumor tissue as well as in the peripheral tumor regions of mice exposed to IL-12 (FIGS. 9A and C, left), while control tumors were limited to strong peripheral localization of V-sense (FIGS. 9B and C, right).

Immune Phenotyping.

Immunosuppressive regulators in the tumor include T regulatory (Treg) and myeloid-derived tumor cells (MDSC). Tregs (CD4$^+$/FoxP3$^+$) and MDSC [CD11b$^+$/Gr-1(Ly6-C/G)$^+$] suppress effective antitumor immune responses. CD4$^+$ and CD8$^+$ T cells are the primary adaptive immune cell mediators within the tumor and the proportion of T cell subsets and DC present in the tumor plays a critical role in tumor rejection (Solheim et al., 2007; Zhao et al., 2012). Preliminary studies show that IL-12 decreases MDSC and increases CD4$^+$ and CD8$^+$ T cells in the tumor 24 hours after treatment (FIG. 10).

REFERENCES

The following references, to the extent that they provide exemplary procedural or other details supplementary to those set forth herein, are specifically incorporated herein in their entirety by express reference thereto:

Mielgo, A. & Schmid, M. C. Impact of tumour associated macrophages in pancreatic cancer. BMB reports 46, 131-138 (2013).

Ahrens, E. T., Young, W. B., Xu. H. & Pusateri, L. K. Rapid quantification of inflammation in tissue samples using perfluorocarbon emulsion and fluorine-19 nuclear magnetic resonance. BioTechniques 50, 229-234 (2011).

Hitchens, T. K., et al. 19F MRI detection of acute allograft rejection with in vivo perfluorocarbon labeling of immune cells. Magnetic resonance in medicine: official journal of the Society of Magnetic Resonance in Medicine/Society of Magnetic Resonance in Medicine 65, 1144-1153 (2011).

Solheim, J. C., et al. Spleen but not tumor infiltration by dendritic and T cells is increased by intravenous adenovirus-Flt3 ligand injection. Cancer gene therapy 14, 364-371 (2007).

Zhao, Y., et al. Hepatic stellate cells produce vascular endothelial growth factor via phospho-p44/42 mitogen-activated protein kinase/cyclooxygenase-2 pathway. Molecular and cellular biochemistry 359, 217-223 (2012).

AUDIBERT. F, "Adjuvants for vaccines, a quest." *Int. Inmunopharmacol.*, 3(8):1187-1193 (2003).

BARNIER-QUER. C et al., "Adjuvant effect of cationic liposomes for subunit influenza vaccine: influence of antigen loading method, cholesterol and immune modulators." *Pharmaceutics*, 5(3):392-410 (2013).

BRAUMULLER, H et al., "T-helper-1-cell cytokines drive cancer into senescence," *Nature*, 494(7437):361-365 (2013).

BREWER, J M. "(How) do aluminium adjuvants work? *Immunol. Lett.*, 102(1):10-15 (2006).

CRAPARO, E F and BONDI, M L, "Application of polymeric nanoparticles in immunotherapy." *Curr. Opin. Allergy Clin. Immunol.*, 12(6):658-664 (2012).

DAFTARIAN, P M et al., "A targeted and adjuvanted nanocarrier lowers the effective dose of liposomal amphotericin B and enhances adaptive immunity in murine cutaneous leishmaniasis," *J. Infect. Dis.*, 208(11):1914-1922 (2013).

DINARELLO. C A. Interleukin 1 and interleukin 18 as mediators of inflammation and the aging process." *Amer. J. Clin. Nutr.*, 83(2):447S-455S (2006).

FACSDIVA Software V6.0, B. B., San Jose. C A, USA (2007).

HALE. W G, and MARGHAM, J P. "*HARPER COLLINS DICTIONARY OF BIOLOGY*," HarperPerennial. New York (1991).

HARDMAN, J G, and LIMBIRD. L E, (Eds.), "*GOODMAN AND GILMAN'S THE PHARMACOLOGICAL BASIS OF THERAPEUTICS*" 10$^{th}$ Edition. McGraw-Hill, New York (2001).

HORNUNG, V et al., "Silica crystals and aluminum salts activate the NALP3 inflammasome through phagosomal destabilization." *Nature Immunol.*, 9(8):847-856 (2008).

JAIME-RAMIREZ, A C et al., "IL-12 enhances the antitumor actions of trastuzumab via NK cell IFN-gamma production," *J. Immunol.*, 186(6):3401-3409 (2011).

KOOL. M et al., "Alum adjuvant boosts adaptive mnununity by inducing uric acid and activating inflammatory dendritic cells," *J. Exp. Med.*, 205(4):869-882 (2008).

LAN, K H et al., "A DNA vaccine against cytotoxic T-lymphocyte associated antigen-4 (CTLA-4) prevents tumor growth," *Biochem. Biophys. Res. Commun.*, 440(2):222-228 (2013).

LOWENSTEIN, C J and PADALKO, E. "iNOS (NOS2) at a glance." *J. Cell Sci.*, 117(Pt 14):2865-2867 (2004).

MANETTI. R et al., "Natural killer cell stimulatory factor (interleukin 12 [IL-12]) induces T helper type 1 (Th1)-specific immune responses and inhibits the development of IL-4-producing Th cells." *J. Exp. Med.*, 177(4):1199-1204 (1993).

MARTINON. F et al., "Gout-associated uric acid crystals activate the NALP3 inflammasome," *Nature*, 440(7081): 237-241 (2006).

MERAZ, I M et al., "Multivalent presentation of MPL by porous silicon microparticles favors T helper 1 polarization enhancing the anti-tumor efficacy of doxorubicin nanoliposomes." *PloS One*, 9(4):e94703 (2014).

MERAZ. I M et al., "Activation of the inflammasome and enhanced migration of microparticle-stimulated dendritic cells to the draining lymph node," *Mol. Pharm.*, 9(7): 2049-2062 (2012).

MERAZ, I M et al., "Adjuvant cationic liposomes presenting MPL and IL-12 induce cell death, suppress tumor growth, and alter the cellular phenotype of tumors in a murine model of breast cancer," *Mol. Pharm.*, 11(10): 3484-3491 (September 2014).

MORI. A et al., "The vaccine adjuvant alum nhibits IL-12 by promoting PI3 kinase signaling while chitosan does not inhibit IL-12 and enhances Th1 and Th17 responses," *Eur. J. Immunol.*, 42(10):2709-2719 (2012).

NAPOLI. C et al., "Effects of nitric oxide on cell proliferation: novel insights." *J. Am. Coil. Cardiol.*, 62(2):89-95 (2013).

NEEDLEMAN, S B and WUNSCH. C D. "A general method applicable to the search for similarities in the amino acid sequence of two proteins." *J. Mol. Biol.*, 48(3):443-453 (1970).

PHAN, G Q and ROSENBERG, S A, "Adoptive cell transfer for patients with metastatic melanoma: the potential and promise of cancer immunotherapy," *Cancer Control*, 20(4):289-297 (2013).

RIMANIOL, A C et al., "In vitro interactions between macrophages and aluminum-containing adjuvants," *Vaccine*, 25(37-38):6784-6792 (2007).

SINGLETON. P and SAINSBURY. D, "DICTIONARY OF MICROBIOLOGY AND MOLECULAR BIOLOGY." $2^{nd}$ Ed., John Wiley and Sons, New York (1987).

SIMPSON-ABELSON, M R et al., "IL-12 delivered intratumorally by multilamellar liposomes reactivates memory T cells in human tumor microenvironments," *Clin. Immunol.*, 132(1):71-82 (2009).

SYPEK. J P et al., "Resolution of cutaneous leishmaniasis: interleukin 12 initiates a protective T helper type 1 immune response," *J. Exp. Med.*, 177(6):1797-1802 (1993).

WAN, S et al., "Chemotherapeutics and radiation stimulate MHC class I expression through elevated interferon-beta signaling in breast cancer cells," *PloS One.* 7(3):e32542 (2012).

WAYTECK, L et al., "A personalized view on cancer immunotherapy," *Cancer Lett.*, 352(1):113-125 (2013).

YAN, W et al., "Mechanism of adjuvant activity of cationic liposome: phosphorylation of a MAP kinase, ERK and induction of chemokines," *Mol. Immunol.*, 44(15):3672-3681 (2007).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the disclosure using terms such as "comprising." "having," "including." or "containing," with reference to an element or elements is intended to provide support for a similar aspect or embodiment of the disclosure that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this disclosure have been described in terms of certain embodiments, it will be apparent to those of ordinary skill in the art that variations may be applied to the compositions and methods and in the steps or in the sequence of steps of the method described herein without departing from the concept, spirit and scope of the disclosure. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the disclosure as defined by the appended claims.

What is claimed is:

1. A cationic liposomal nanoparticle comprising: one or more distinct lipids and i) one or more toll-like 4 receptor (TLR-4) ligands, and ii) interleukin-12 (IL-12) on or about the nanoparticle outer surface.

2. The cationic liposomal nanoparticle of claim 1, further comprising at least one cellular-targeting moiety comprising a chemical targeting moiety, a physical targeting moiety, a ligand moiety, a ligand targeting moiety, a geometrical targeting moiety, or any combination thereof.

3. The cationic liposomal nanoparticle of claim 2, wherein the at least one cellular-targeting moiety comprises a plurality of distinct antigens to elicit one or more target-specific immune responses.

4. The cationic liposomal nanoparticle of claim 1, further comprising an imaging agent, a contrast agent, a radiolabel, a chemotherapeutic agent, a targeting agent, or any combination thereof.

5. The cationic liposomal nanoparticle of claim 1, further comprising at least one moiety selected from the group consisting of a ligand, a dendrimer, an oligomer, an aptamer, a binding protein, an antibody, an antigen binding fragment thereof, a biomolecule, or any combination thereof.

6. The cationic liposomal nanoparticle of claim 1, wherein the at least one outer surface further comprises one or more dendritic cells, one or more cytokines, or any combination thereof.

7. The cationic liposomal nanoparticle of claim 1, admixed with one or more pharmaceutically-acceptable carriers, diluents, excipients, or any combination thereof.

8. The cationic liposomal nanoparticle of claim 1, formulated with one or more antineoplastic agents, one or more other cytotoxic agents, one or more cytostatic agents, or one or more therapeutic or chemotherapeutic agents, or any combination thereof.

9. The cationic liposome of claim 1, which is composed of DOTAP, DPPC, or cholesterol, or any combination thereof.

10. A composition comprising the cationic liposomal nanoparticle of claim 1, and a pharmaceutical buffer, a diluent, an excipient, a vehicle, or any combination thereof.

11. The composition of claim 10 comprising an isolated population of mammalian cells comprising the cationic liposomal nanoparticle.

12. A method of treating breast cancer in a human subject, comprising administering to a human subject in need thereof, an effective amount of the composition of claim 10.

13. The cationic liposomal nanoparticle of claim 1 wherein the one or more TLR4 ligands comprises monophosphoryl lipid A (MPL-A).

\* \* \* \* \*